United States Patent
Öörni et al.

(10) Patent No.: US 11,442,072 B2
(45) Date of Patent: Sep. 13, 2022

(54) METHOD FOR MEASURING LDL AGGREGATION

(71) Applicant: Jenny and Antti Wihuri Foundation, Helsinki (FI)

(72) Inventors: Katariina Öörni, Vantaa (FI); Maija Ruuth, Espoo (FI); Petri Kovanen, Espoo (FI)

(73) Assignee: Jenny and Antti Wihuri Foundation, Helsinki (FI)

( * ) Notice: Subject to any disclaimer, the term of this patent is extended or adjusted under 35 U.S.C. 154(b) by 476 days.

(21) Appl. No.: 16/459,524

(22) Filed: Jul. 1, 2019

(65) Prior Publication Data

US 2020/0025779 A1 Jan. 23, 2020

Related U.S. Application Data

(60) Provisional application No. 62/696,154, filed on Jul. 10, 2018.

(51) Int. Cl.
| | |
|---|---|
| *G01N 33/92* | (2006.01) |
| *C12Q 1/44* | (2006.01) |
| *C12Q 1/60* | (2006.01) |
| *A61K 45/06* | (2006.01) |

(52) U.S. Cl.
CPC .............. *G01N 33/92* (2013.01); *C12Q 1/44* (2013.01); *C12Q 1/60* (2013.01); *A61K 45/06* (2013.01)

(58) Field of Classification Search
CPC ...................................................... A23L 33/40
See application file for complete search history.

(56) References Cited

PUBLICATIONS

[No Author Listed], "World Medical Association Declaration of Helsinki: ethical principles for medical research involving human subjects," JAMA, 2013, 310(20):2191-4.
Acessdata.fda [online], "CFR—Code of Federal Regulations Title 21," Apr. 1, 2019, retrieved on Oct. 15, 2019, retrieved from URL https://www.accessdata.fda.gov/scripts/cdrh/cfdocs/cfcfr/CFRSearch.cfm?fr=101.83, 4 pages.
Aromaa et al., "Health and functional capacity in Finland: Baseline results of the Health 2000 health examination survey," Publications of the National Public Health Institute, 2004, B12/200, 175 pages.
Baruch et al., "Effects of RG7652, a Monoclonal Antibody Against PCSK9, on LDL-C, LDL-C Subfractions, and Inflammatory Biomarkers in Patients at High Risk of or With Established Coronary Heart Disease (from the Phase 2 EQUATOR Study)," Am J Cardiol, 2017, 119: 1576-1583.
Benecol.co.us [online], "Our Products," 2019, retrieved on Oct. 14, 2019, retrieved from URL https://www.benecol.co.uk/our-products, 5 pages.
Cater N. B., "Plant Stanol Ester: Review of Cholesterol-Lowering Efficacy and Implications for Coronary Heart Disease Risk Reduction," Preventative Cardiology, 2000, 3(3):121-130.
ClinicalTrials.gov [online], "Exenatide and Brown Adipose Tissue (exe01)," Dec. 26, 2016, retrieved Oct. 14, 2019, retrieved from URL https://clinicaltrials.gov/ct2/show/record/NCT03002675?term=NCT03002675&rank=1, 7 pages.
ClinicalTrials.gov [online], "Effects of Plant Stanol Esters on Blood Flow (Blood Flow)," Aug. 28, 2013, retrieved Oct. 15, 2019, retrieved from URL https://clinicaltrials.gov/ct2/show/record/NCT01315964?term=NCT01315964&rank=1, 6 pages.
ClinicalTrials.gov [online], "Effects of Overfeeding Followed by Weight Loss on Liver Fat Content and Adipose Tissue Inflammation)," May 7, 2014, retrieved Oct. 15, 2019, retrieved from URL https://clinicaltrials.gov/ct2/show/record/NCT0213 3144?term=NCT0213 3144&rank=1, 8 pages.
Folch et al., "A simple method for the isolation and purification of total lipids from animal tissues," J Biol Chem, 1957, 226: 497-509.
Guarino et al., "Aggregation kinetics of low density lipoproteins upon exposure to sphingomyelinase," Journal of Colloid and Interface Science, 2004, 279(1): 109-116.
Guarino et al., "Sphingomyelinase-to-LDL molar ratio determines low density lipoprotein aggregation size: biological significance," Chemistry and Physics of Lipids, 2006, 142:3 3-42.
Gylling, H., et al., "The effects of plant stanol ester consumption on arterial stiffness and endothelial function in adults: a randomized controlled clinical trial," BMC Cardiovasc Disord, 2013, 13(1):13-50.
Haimi et al., "Software tools for analysis of mass spectrometric lipidome data," Anal Chem, 2006, 78:8324-8331.
Hallberg et al., "Lipoprotein fractionation in deuterium oxide gradients: a procedure for evaluation of antioxidant binding and susceptibility to oxidation," J Lipid Res, 1994, 35(1): 1-9.
Havel et al., "The distribution and chemical composition of ultra-centrifugally separated lipoproteins in human serum," J Clin Invest, 1955, 34: 1345-1355.
Houjou et al., "Rapid and selective identification of molecular species in phosphatidylcholine and sphingomyelin by conditional neutral loss scanning and MS3," Rapid Commun Mass Spectrom, 2004, 18: 3123-3130.
Hsu et al., "Structural determination of glycosphingolipids as lithiated adducts by electrospray ionization mass spectrometry using low-energy collisional-activated dissociation on a triple stage quadrupole instrument," J Am Soc Mass Spectrom, 2001, 12: 61-79.
Kauhanen et al., "Development and validation of a high-throughput LC-MS/MS assay for routine measurement of molecular ceramides," Anal Bioanal Chem, 2016, 408: 3475-3483.
Laajala et al., "Optimized design and analysis of preclinical intervention studies in vivo," Sci Rep, 2016, 6:30723.
Luukkonen et al., "Saturated Fat Is More Metabolically Harmful for the Human Liver Than Unsaturated Fat or Simple Sugars," Diabetes Care, 2018, 41(8):1732-1739.
Magnusdottir et al., "Plasma alkylresorcinols reflect important whole-grain components of a healthy Nordic diet," J Nutr, 2013, 143: 1383-1390.

(Continued)

*Primary Examiner* — Bin Shen
(74) *Attorney, Agent, or Firm* — Fish & Richardson P.C.

(57) ABSTRACT

The present disclosure relates to a method for measuring aggregation of low-density lipoprotein (LDL). The susceptibility of LDL to aggregate is an important factor regarding prognosis, diagnosis and surveillance of atherosclerotic cardiovascular diseases and cardiometabolic diseases, such as type 2 diabetes and related conditions, at various stages of their development. Also provided are methods of treatment of such diseases in subjects in need thereof.

18 Claims, 29 Drawing Sheets

Specification includes a Sequence Listing.

(56) References Cited

PUBLICATIONS

Nguyen et al., "Spontaneous remodeling of HDL particles at acidic pH enhances their capacity to induce cholesterol efflux from human macrophage foam cells," J Lipid Res., 2012, 53:2115-2125.

Ruuth et al., "Susceptibility of low-density lipoprotein particles to aggregate depends on particle lipidome, is modifiable, and associates with future cardiovascular deaths," Eur Heart J, 2018, 39(27):2562-2573.

Sneck et al., "Conformational changes of apoB-100 in SMase-modified LDL mediate formation of large aggregates at acidic pH," J Lipid Res., 2012, 53:1832-1839.

Uusitupa et al., "Effects of an isocaloric healthy Nordic diet on insulin sensitivity, lipid profile and inflammation markers in metabolic syndrome—a randomized study (Sysdiet)," J Intern Med, 2013, 274:52-66.

| | Total cholesterol | ApoAI | ApoAII | ApoB | HDL-C | LDL-C | Lp(a) | Lp PLA2 | LDL size | CRP |
|---|---|---|---|---|---|---|---|---|---|---|
| Aggregate size at 2 h | -0.186 | -0.054 | -0.128 | -0.221 | 0.108 | -0.167 | -0.012 | -0.036 | -0.001 | -0.043 |
| Total cholesterol | | 0.334˙ | 0.459˙˙ | 0.910˙˙ | 0.427˙˙ | 0.928˙˙ | 0.097 | 0.633˙˙ | 0.455˙˙ | 0.084 |
| ApoA-I | | | 0.783˙˙ | .068 | 0.898˙˙ | 0.120 | -0.194 | -0.138 | -0.026 | -0.481˙˙ |
| ApoA-II | | | | .245 | 0.649˙˙ | 0.261 | -0.072 | 0.048 | -0.010 | -0.373˙˙ |
| ApoB | | | | | 0.153 | 0.900˙˙ | 0.133 | 0.687˙˙ | 0.379˙ | 0.234 |
| HDL-C | | | | | | 0.267 | -0.062 | -0.085 | 0.208 | -0.379˙˙ |
| LDL-C | | | | | | | 0.161 | 0.686˙˙ | 0.573˙˙ | 0.201 |
| Lp(a) | | | | | | | | 0.079 | 0.163 | 0.154 |
| Lp-PLA2 | | | | | | | | | 0.511˙˙ | 0.263 |
| LDL size | | | | | | | | | | 0.038 |

Figure 6

METHOD FOR MEASURING LDL AGGREGATION

CROSS-REFERENCE TO RELATED APPLICATION

This application claims priority to U.S. Provisional Appl. No. 62/696,154, filed Jul. 10, 2018, the contents of which are incorporated by reference herein in its entirety.

FIELD

The present disclosure relates in part to a method for measuring aggregation of low-density lipoprotein (LDL). The susceptibility of LDL to aggregate is an important factor regarding prognosis, diagnosis and surveillance of atherosclerotic cardiovascular diseases and cardiometabolic diseases, such as type 2 diabetes and related conditions, at various stages of their development.

BACKGROUND

There is universal agreement that cholesterol is a key lipid constituent of cell membranes. Cholesterol is essential for normal growth and viability of most higher organisms. However, too much serum cholesterol has been correlated with life-threatening lipid related diseases atherosclerotic cardiovascular diseases, notably coronary heart disease, stroke, and peripheral arterial disease. An elevated plasma concentration of low-density lipoprotein cholesterol (LDL-C) is shown to be a primary causal factor in the development of atherosclerotic cardiovascular disease (ASCVD). Statins are a group of medicines that are used to lower the level of LDL-C in the circulating blood plasma. However, even after efficient LDL-C-lowering, a substantial residual risk for ASCVD events remains.

Atherosclerosis arises from subendothelial retention, or trapping, of LDL within the inner layer of the arterial wall, the intima, and several steps are required for plasma LDL-C to provoke normal arteries to become diseased. In the intima, the retained lipoproteins become modified by arterial-wall enzymes and oxidants. The modified lipoproteins tend to aggregate, and aggregated lipoprotein-derived particles are found both in human and in experimentally induced atherosclerotic lesions in animal models of atherosclerosis. The local processes triggering aggregation of LDL particles in the arterial intima include lipid peroxidation and proteolytic and lipolytic digestion of LDL by local enzymes, such as the mast cell chymase having chymotrypsin-like activity, the group V secretory phospholipase A2 (PLA2), which is produced by macrophages, as well as the secretory sphingomyelinase (SMase), which is released by macrophages and endothelial cells of the atherosclerosis-susceptible arterial segments. Aggregation enhances the binding of lipoproteins to the arterial extracellular matrix, and the large size of lipoprotein aggregates makes their return to the circulating blood across the endothelium nearly impossible. Moreover, aggregated LDL induces the formation of foam cells, a hallmark of atherosclerotic lesions at all stages of atherogenesis. Indeed, the development of an atherosclerotic lesion results from a series of maladaptive inflammatory response of innate and adaptive immune cells to the retained, modified, and aggregated lipoprotein-derived material.

Guarino et al. 2004 (Journal of Colloid and Interface Science 279; 109-116) have shown that sphingomyelinase and pH contribute for the aggregation kinetics of LDLs in vitro. In this cited study, dynamic light scattering and UV-vis absorbance spectroscopy were used to measure aggregation kinetics and particle sizes of LDL aggregates.

Sneck et al. 2012 (J Lipid Res. 53(9); 1832-9) have shown that the lower the pH, the higher is the degree of aggregation of identically lipolyzed LDL particles and the greater is the size of the aggregates formed.

Guarino et al. 2006 (Chemistry and Physics of Lipids 142; 33-42) have shown that that the extent of LDL aggregation can be determined by the molar ratio of sphingomyelinase (SMase)-to-LDL rather than their absolute concentrations. Dynamic light scattering was used to measure aggregation kinetics and particle sizes of LDL aggregates.

Current methods for the assessment of cardiovascular risk are based on measurement of plasma lipoproteins (cholesterol and triglycerides) and of inflammatory markers (notably the high sensitivity C reactive protein). However, a significant number of cardiovascular events occur in subjects, either statin-naive or statin users, in whom the levels of all of the above-mentioned risk parameters are within the optimal range. Thus, a residual cardiovascular risk prevails. Therefore, novel methods to provide critical incremental information to the systematic cardiovascular risk estimation of a person at risk and to recognize the persons needing a medication are still needed.

BRIEF SUMMARY

A significant number of cardiovascular events occur in subjects in whom the levels of all currently used risk parameters are within the optimal range. An advantage of the method of the disclosure is that the determination of LDL aggregation that is found to be an important factor in arterial lipid accumulation, atherosclerotic plaque inflammation, and even plaque rupture, can be used to the systematic cardiovascular risk estimation of a person at risk. Thus, based on the methods described herein one can modify, tailor, or select appropriate treatments for subjects having or at risk of developing an atherosclerotic cardiovascular disease or a cardiometabolic disease.

The object of the disclosure is achieved by a method which is characterized by what is stated in the independent claims. The preferred embodiments of the disclosure are disclosed in the dependent claims.

One object of the present disclosure is a method comprising: providing LDL particles from a human blood plasma or serum sample; mixing the LDL particles with a sphingomyelinase enzyme in a solution at acidic pH; detecting formation of LDL aggregates in the solution, and measuring the size of the detected LDL aggregates (e.g., by DLS). In certain instances, the size of the LDL aggregates is measured every 15 to 30 minutes for up to 6 hours after addition of the sphingomyelinase enzyme. In certain instances, the size of the LDL aggregates is measured about 2 hours (e.g., 1 hr 45 min, 1 hr 50 min, 1 hr 55 min, 2 hr, 2 hr 5 min, 2 hr 10 min, 2 hr 15 min) after addition of the sphingomyelinase enzyme.

Another object of the present disclosure is a method comprising: providing a human plasma or serum sample; mixing the human plasma or serum sample with a sphingomyelinase enzyme at acidic pH; detecting formation of LDL aggregates in the sample, and measuring the size of the detected LDL aggregates (e.g., by DLS). In certain instances, the size of the LDL aggregates is measured every 15 to 30 minutes for up to 6 hours after addition of the sphingomyelinase enzyme. In certain instances, the size of the LDL aggregates is measured about 2 hours after addition of the sphingomyelinase enzyme.

Another object of the present disclosure is a method comprising: providing a human plasma or serum sample; isolating LDL particles from the human plasma or serum sample (e.g., by ultracentrifugation (e.g., sequential $D_2O$ ultracentrifugation); mixing the isolated LDL particles with a sphingomyelinase enzyme at acidic pH; detecting formation of LDL aggregates in the sample, and measuring the size of the detected LDL aggregates (e.g., by DLS). In certain instances, the size of the LDL aggregates is measured every 15 to 30 minutes for up to 6 hours after addition of the sphingomyelinase enzyme. In certain instances, the size of the LDL aggregates is measured about 2 hours after addition of the sphingomyelinase enzyme.

Still another object of the present disclosure is a method of treating an atherosclerotic cardiovascular disease or a cardiometabolic disease in a human subject in need thereof, the method comprising administering to the human subject a therapeutically effective amount of a cholesterol lowering medication, wherein LDL particles from a blood plasma or serum sample of the human subject upon treatment with sphingomyelinase enzyme at acidic pH has been determined to form LDL aggregates that have a median size of at least 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1050 nm, 1100 nm, 1150 nm, 1200 nm, 1250 nm, 1300 nm, 1350 nm, 1400 nm, 1450 nm, 1500 nm, 1550 nm, 1600 nm, 1650 nm, 1700 nm, 1750 nm, 1800 nm, 1850 nm, 1900 nm, 1950 nm, 2000 nm, 2050 nm, 2100 nm, 2150 nm, 2200 nm, 2250 nm, 2300 nm, 2350 nm, 2400 nm, 2450 nm, 2500 nm, 2550 nm, 2600 nm, 2650 nm, 2700 nm, 2750 nm, 2800 nm, 2850 nm, 2900 nm, 2950 nm, or 3000 nm. In one instance, the LDL aggregates have a median size in range of 200 nm to 3000 nm. In some instances, the surface of the LDL particles of the human subject have a higher proportion of total SM and/or a lower proportion of total PC relative to a human subject (e.g., of the same ethnicity) that does not have ASCVD.

Still another object of the present disclosure is a method of treating an atherosclerotic cardiovascular disease or a cardiometabolic disease in a human subject in need thereof, the method comprising administering to the human subject a therapeutically effective amount of a cholesterol lowering medication, wherein LDL particles from a blood plasma or serum sample of the human subject upon treatment with sphingomyelinase enzyme at acidic pH has been determined to form LDL aggregates that have a median size in range of 200 nm to 400 nm, 400 nm to 600 nm, 600 nm to 800 nm, 800 nm to 1000 nm, 1000 nm to 1200 nm, 1200 nm to 1400 nm, 1400 nm to 1600 nm, 1600 nm to 1800 nm, 1800 nm to 2000 nm, 2000 nm to 2200 nm, 2200 nm to 2400 nm, 2400 nm to 2600 nm, 2600 nm to 2800 nm, or 2800 nm to 3000 nm. In one instance, the LDL aggregates have a median size in range of 200 nm to 2000 nm. In one instance, the LDL aggregates have a median size in range of 200 nm to 3000 nm. In some instances, the surface of the LDL particles of the human subject have a higher proportion of total SM and/or a lower proportion of total PC relative to a human subject (e.g., of the same ethnicity) that does not have ASCVD.

Also provided is a method of treating an atherosclerotic cardiovascular disease or a condition associated with LDL aggregation in a human subject in need thereof, the method comprising administering to the human subject a therapeutically effective amount of a cholesterol lowering medication, wherein LDL particles from a blood plasma or serum sample of the human subject upon treatment with sphingomyelinase enzyme at acidic pH has been determined to form LDL aggregates that have a median size of at least 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1050 nm, 1100 nm, 1150 nm, 1200 nm, 1250 nm, 1300 nm, 1350 nm, 1400 nm, 1450 nm, 1500 nm, 1550 nm, 1600 nm, 1650 nm, 1700 nm, 1750 nm, 1800 nm, 1850 nm, 1900 nm, 1950 nm, 2000 nm, 2050 nm, 2100 nm, 2150 nm, 2200 nm, 2250 nm, 2300 nm, 2350 nm, 2400 nm, 2450 nm, 2500 nm, 2550 nm, 2600 nm, 2650 nm, 2700 nm, 2750 nm, 2800 nm, 2850 nm, 2900 nm, 2950 nm, or 3000 nm. In one instance, LDL aggregates that have a median size of at least 200 nm. In one instance, the LDL aggregates have a median size in range of 200 nm to 3000 nm. In one instance, the LDL aggregates have a median size in range of 200 nm to 3000 nm. In some instances, the surface of the LDL particles of the human subject have a higher proportion of total SM and/or a lower proportion of total PC relative to a human subject (e.g., of the same ethnicity) that does not have ASCVD. In some instances, the human subject is a Caucasian individual. In other instances, the human subject is an African-American individual. In other instances, the human subject is an East Asian individual. In other instances, the human subject is a South Asian individual. In certain instances, the cholesterol lowering medication is a statin, a healthy diet (e.g., a healthy Nordic diet, a healthy Mediterranean diet) a low sucrose diet, a PCSK9 inhibitor, a HMG CoA reductase inhibitor, a selective cholesterol absorption inhibitor, a bile-acid binding resin, a plant stanol, a plant stanol ester, or combinations thereof. In some instances, the human subject is administered a statin or a PCSK9 inhibitor along with a food (e.g., yogurt, yogurt drink, spread, bars, chews), diet, or supplement containing plant stanol ester (e.g., about 1.0 to 3 grams per day (e.g., 1.5 to 2.4 g/day; or 2 g/day)). In certain instances, the human subject is administered a statin or a PCSK9 inhibitor along with a diet or supplement containing plant stanol ester (e.g., about 2 grams per day) and a diet low in saturated fat.

Also featured is a method of treating an atherosclerotic cardiovascular disease or a condition associated with LDL aggregation in a human subject in need thereof, the method comprising administering to the human subject a therapeutically effective amount of a cholesterol lowering medication, wherein LDL particles from a blood plasma or serum sample of the human subject upon treatment with sphingomyelinase enzyme at acidic pH has been determined to form LDL aggregates that have a median size in range of 200 nm to 400 nm, 400 nm to 600 nm, 600 nm to 800 nm, 800 nm to 1000 nm, 1000 nm to 1200 nm, 1200 nm to 1400 nm, 1400 nm to 1600 nm, 1600 nm to 1800 nm, 1800 nm to 2000 nm, 2000 nm to 2200 nm, 2200 nm to 2400 nm, 2400 nm to 2600 nm, 2600 nm to 2800 nm, or 2800 nm to 3000 nm. In one instance, the LDL aggregates have a median size in range of 200 nm to 3000 nm. In some instances, the surface of the LDL particles of the human subject have a higher proportion of total SM and/or a lower proportion of total PC relative to a human subject (e.g., of the same ethnicity) that does not have ASCVD. In some instances, the human subject is a Caucasian individual. In other instances, the human subject is an African-American individual. In other instances, the human subject is an East Asian individual. In other instances, the human subject is a South Asian individual. In certain instances, the cholesterol lowering medication is a statin, a healthy Nordic diet, a low sucrose diet, a PCSK9 inhibitor, a HMG CoA reductase inhibitor, a selective cholesterol absorption inhibitor, a bile-acid binding resin, a plant stanol, a plant stanol ester, or combinations thereof. In some instances, the human subject is administered a statin or a PCSK9 inhibitor along with a food (e.g., yogurt, yogurt drink, spread, bars, chews), diet, or supplement containing plant stanol ester (e.g., about 1.0 to 3 grams per day (e.g., 1.5 to 2.4 g/day; or 2 g/day)). In certain instances, the human subject is administered a statin or a PCSK9 inhibitor along with a food (e.g., yogurt, yogurt drink, spread, bars, chews), diet, or supplement containing plant stanol ester (e.g., about 1.0 to 3 grams per day (e.g., 1.5 to 2.4 g/day; or 2 g/day)) and a diet low in saturated fat.

This disclosure also features a method of treatment, the method comprising identifying a patient as having a condition associated with LDL aggregation and administering to the patient a therapeutically effective amount of a cholesterol lowering medication, wherein the patient is, or has been previously been, determined to have LDL aggregates that have a median size in range of at least 200 nm (e.g., 200 nm to 3500 nm) when assayed after LDL particles from a blood plasma or serum sample of the patient are/were mixed with sphingomyelinase enzyme at acidic pH (e.g., measured about 2 hours after sphingomyelinase enzyme addition). In some instances, the condition associated with LDL aggregation is ASCVD. In some instances, the condition associated with LDL aggregation is a cardiometabolic disease (e.g., type 2 diabetes or a related condition). In some instances, the patient is a Caucasian individual. In other instances, the patient is an African-American individual. In other instances, the patient is an East Asian individual. In other instances, the patient is a South Asian individual. In certain instances, the cholesterol lowering medication is a statin, a healthy Nordic diet, a low sucrose diet, a PCSK9 inhibitor, a HMG CoA reductase inhibitor, a selective cholesterol absorption inhibitor, a bile-acid binding resin, a plant stanol, a plant stanol ester, or combinations thereof. In some instances, the patient is administered a statin or a PCSK9 inhibitor along with a food (e.g., yogurt, yogurt drink, spread, bars, chews), diet, or supplement containing plant stanol ester (e.g., about 1.0 to 3 grams per day (e.g., 1.5 to 2.4 g/day; or 2 g/day)). In certain instances, the patient is administered a statin or a PCSK9 inhibitor along with a food (e.g., yogurt, yogurt drink, spread, bars, chews), diet, or supplement containing plant stanol ester (e.g., about 1.0 to 3 grams per day (e.g., 1.5 to 2.4 g/day; or 2 g/day)) and a diet low in saturated fat.

This disclosure also relates to a method of treatment, the method comprising identifying a patient as having, or at risk of developing, a condition associated with LDL aggregation and administering to the patient a therapeutically effective amount of a cholesterol lowering medication, wherein the patient is, or has been previously been, determined to (i) have LDL aggregates that have a median size in range of at least 200 nm (e.g., 200 nm to 3500 nm) when assayed after LDL particles from a blood plasma or serum sample of the patient are/were mixed with sphingomyelinase enzyme at acidic pH (e.g., measured about 2 hours after sphingomyelinase enzyme addition); and (ii) wherein the surface of the LDL particles of the patient have a higher proportion of total SM and/or a lower proportion of total PC relative to a human subject (e.g., of the same ethnicity) that does not have a condition associated with LDL aggregation (e.g., ASCVD). In some instances, the condition associated with LDL aggregation is ASCVD. In some instances, the condition associated with LDL aggregation is a cardiometabolic disease (e.g., type 2 diabetes or a related condition). In some instances, the patient is a Caucasian individual. In other instances, the patient is an African-American individual. In other instances, the patient is an East Asian individual. In other instances, the patient is a South Asian individual. In certain instances, the cholesterol lowering medication is a statin, a healthy Nordic diet, a low sucrose diet, a PCSK9 inhibitor, a HMG CoA reductase inhibitor, a selective cholesterol absorption inhibitor, a bile-acid binding resin, a plant stanol, a plant stanol ester, or combinations thereof. In some instances, the patient is administered a statin or a PCSK9 inhibitor along with a food (e.g., yogurt, yogurt drink, spread, bars, chews), diet, or supplement containing plant stanol ester (e.g., about 1.0 to 3 grams per day (e.g., 1.5 to 2.4 g/day; or 2 g/day)). In certain instances, the patient is administered a statin or a PCSK9 inhibitor along with a diet or supplement containing plant stanol ester (e.g., about 2 grams per day) and a diet low in saturated fat.

This disclosure also relates to a method of treatment, the method comprising identifying a patient as having, or at risk of developing, a condition associated with LDL aggregation and administering to the patient 0.5 g to 4 g (e.g., 0.5, 1.0, 1.5, 1.6, 1.7, 1.8, 1.9, 2.0, 2.2, 2.4, 2.5, 2.6, 2.7, 2.8, 2.9, 30, 3.5, 4.0 g) of a plant stanol ester daily, wherein the patient is, or has been previously been, determined to have LDL aggregates that have a median size in range of at least 200 nm (e.g., 200 nm to 3500 nm) when assayed after LDL particles from a blood plasma or serum sample of the patient are/were mixed with sphingomyelinase enzyme at acidic pH (e.g., measured about 2 hours after sphingomyelinase enzyme addition); and/or wherein the surface of the LDL particles of the patient have a higher proportion of total SM and/or a lower proportion of total PC relative to a human subject (e.g., one of the same or similar ethnicity and/or the same or similar age; and/or the same sex) that does not have ASCVD. In some instances, the condition associated with LDL aggregation is ASCVD. In some instances, the condition associated with LDL aggregation is a cardiometabolic disease (e.g., type 2 diabetes or a related condition). In some instances, the patient is a Caucasian individual. In other instances, the patient is an African-American individual. In other instances, the patient is an East Asian individual. In other instances, the patient is a South Asian individual. In some instances, the subject is also administered another means for lowering cholesterol (e.g., a statin, a healthy Nordic diet, a low sucrose diet, a PCSK9 inhibitor, a HMG CoA reductase inhibitor, a selective cholesterol absorption inhibitor, a bile-acid binding resin, or combinations thereof). In certain instances, the patient is also on a low saturated fat diet.

This disclosure also features a method of treatment, the method comprising identifying a patient having one or more of the following features: (i) LDL aggregates that have a median size in range of at least 200 nm (e.g., 200 nm to 3500 nm) when assayed after LDL particles from a blood plasma or serum sample of the patient were mixed with sphingomyelinase enzyme at acidic pH (e.g., measured about 2 hours after sphingomyelinase enzyme addition); (ii) a higher proportion of total SM and/or a lower proportion of total PC on the surface of the LDL particles of the patient relative to a human subject (e.g., of the same or similar ethnicity and/or same or similar age and/or same sex) that does not have ASCVD; (iii) a higher body fat percentage than a subject (e.g., one of the same or similar ethnicity and/or the same or similar age; and/or the same sex) without ASCVD; (iv) a South Asian ancestry or ethnicity; and administering to the patient a therapeutically effective amount of a cholesterol lowering medication, In some instances, the subject the cholesterol lowering medication is a statin, a healthy Nordic diet, a low sucrose diet, a low saturated fat diet, a PCSK9 inhibitor, a HMG CoA reductase inhibitor, a selective cholesterol absorption inhibitor, a bile-acid binding resin, a plant stanol ester-containing product, or combinations thereof). In certain instances, the patient is administered about 1 to 3 g/daily (e.g., about 2 g daily) of a plant stanol ester. In certain instances, the patient is administered about 1 to 3 g/daily (e.g., about 2 g daily) of a plant stanol ester and a statin or a PCSK9 inhibitor. In certain instances, the patient is administered 1 to 3 g/daily (e.g., about 2 g daily) of a plant stanol ester, a statin or a PCSK9 inhibitor, and a low saturated fat diet.

One object of the present disclosure is a method of treatment comprising: providing LDL particles from a human blood plasma sample of a human subject; mixing the LDL particles with sphingomyelinase enzyme in a solution at acidic pH; detecting formation of LDL aggregates in said solution; measuring the size of the detected LDL aggregates, and administering to the human subject a therapeutically effective amount of a cholesterol lowering medication.

A method comprising: providing a human serum sample; mixing the human serum sample with a sphingomyelinase enzyme at acidic pH; detecting formation of LDL aggregates in the sample, measuring the size of the detected LDL aggregates, and administering to the human subject a therapeutically effective amount of a cholesterol lowering medication is one object of the present disclosure.

According to the present disclosure is a method comprising: providing LDL particles from a human blood plasma sample of a human subject that has been taking a HMG CoA reductase inhibitor, a selective cholesterol absorption inhibitor, or a bile-acid binding resin; mixing the LDL particles with sphingomyelinase enzyme in a solution at acidic pH; detecting formation of LDL aggregates in said solution; measuring the size of the detected LDL aggregates; and if the LDL aggregates have a median size of at least 500 nm, continue administering to the human subject a therapeutically effective amount of the HMG CoA reductase inhibitor, selective cholesterol absorption inhibitor, or bile-acid binding resin; and if the LDL aggregates have a median size of below 500 nm, discontinue administration to the human subject a therapeutically effective amount of the HMG CoA reductase inhibitor, selective cholesterol absorption inhibitor, or bile-acid binding resin and administer a medication selected from the group consisting of a healthy (Nordic) diet, a low sucrose diet, a low saturated fat diet (e.g., A Nordic diet, a Mediterranean diet), and a PCSK9 inhibitor, or continue administering to the human subject a therapeutically effective amount of the cholesterol lowering medication in combination with a medication selected from the group consisting of a healthy (Nordic) diet, a low sucrose diet, a low saturated fat diet, a PCSK9 inhibitor, and a plant stanol, or a plant stanol ester.

BRIEF DESCRIPTION OF THE DRAWINGS

FIG. 6. Spearman correlation coefficients of aggregate size at 2 h with clinical parameters measured in the Corogene study. * indicates P-value <0.05, and ** indicated P-value <0.01.

SEQUENCE LISTING

Figure 1A:
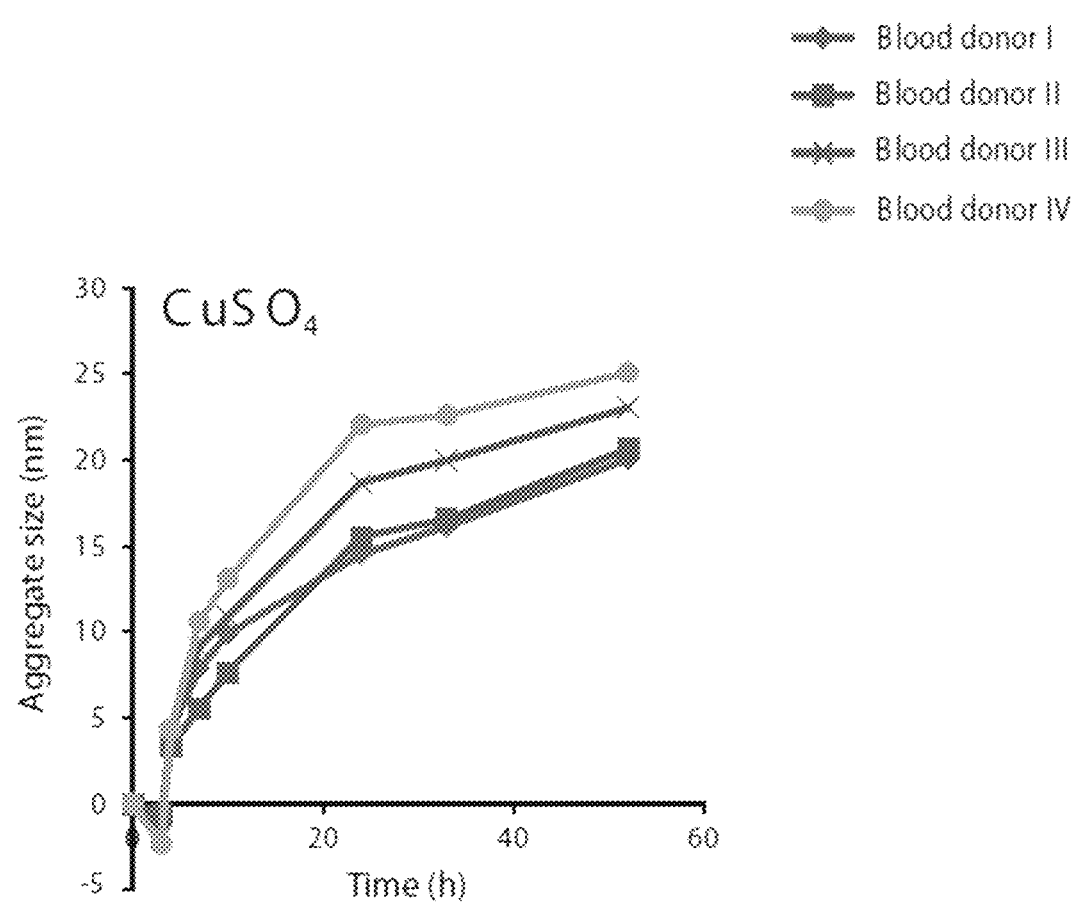
FIG. 1A. Aggregation of LDL induced by oxidation. LDL from four blood donors was incubated with copper sulfate for the indicated times. Aggregation was followed by dynamic light scattering (DLS).
Figure 1B:
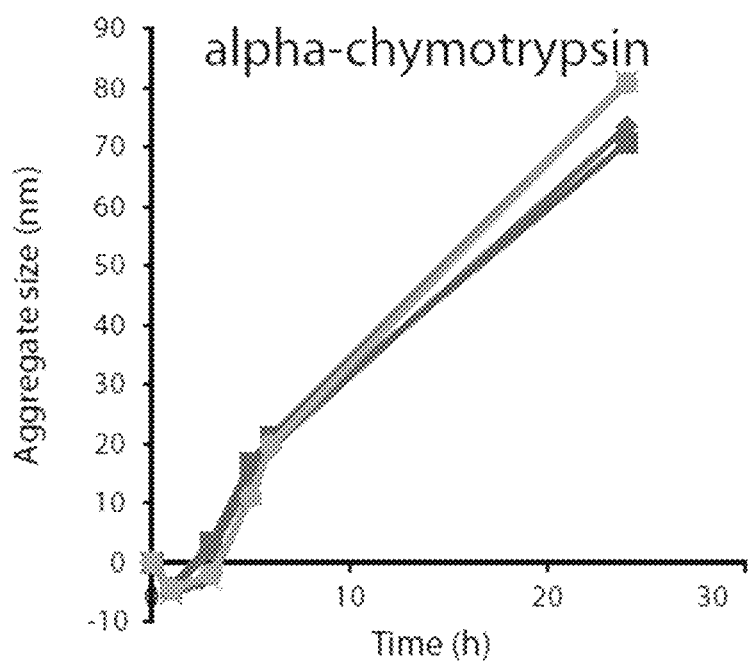
FIG. 1B. Aggregation of LDL induced by proteolysis. LDL from four blood donors was incubated with α-chymotrypsin for the indicated times. Aggregation was followed by DLS.
Figure 1C:
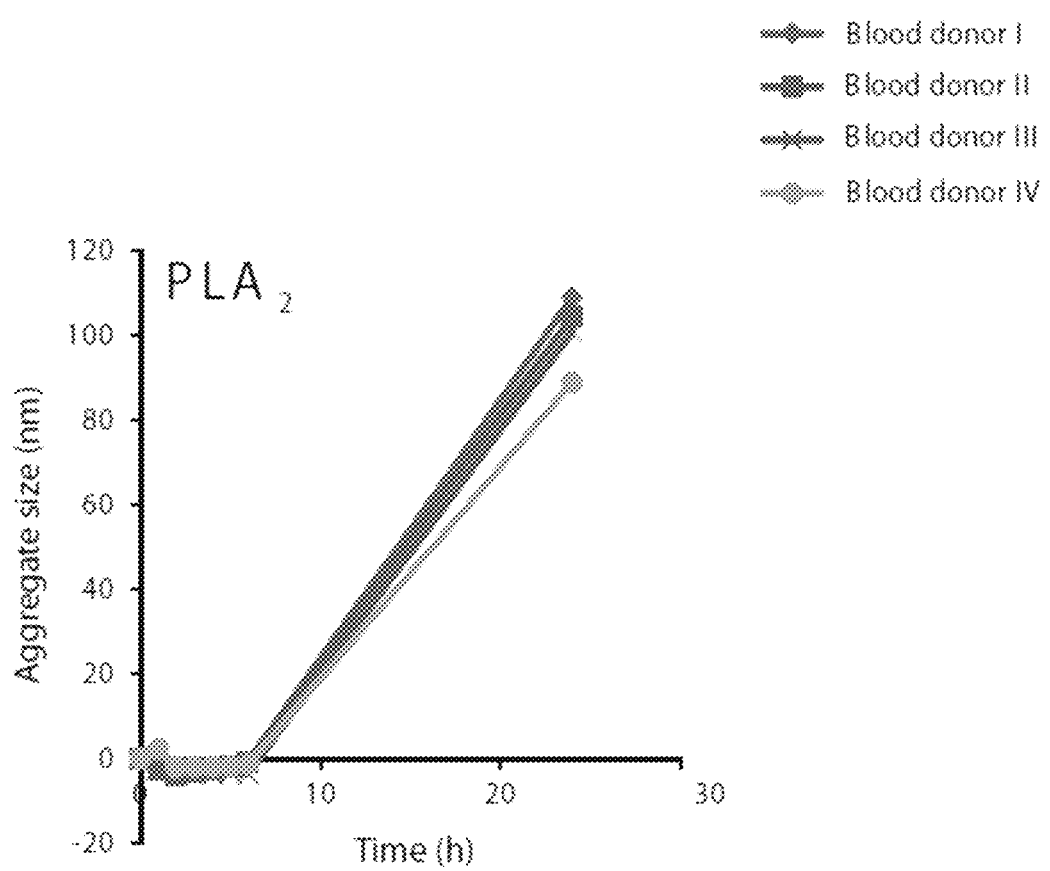
FIG. 1C. Aggregation of LDL induced by phospholipolysis. LDL from four blood donors was incubated with $PLA_2$ for the indicated times. Aggregation was followed by DLS.
Figure 1D:
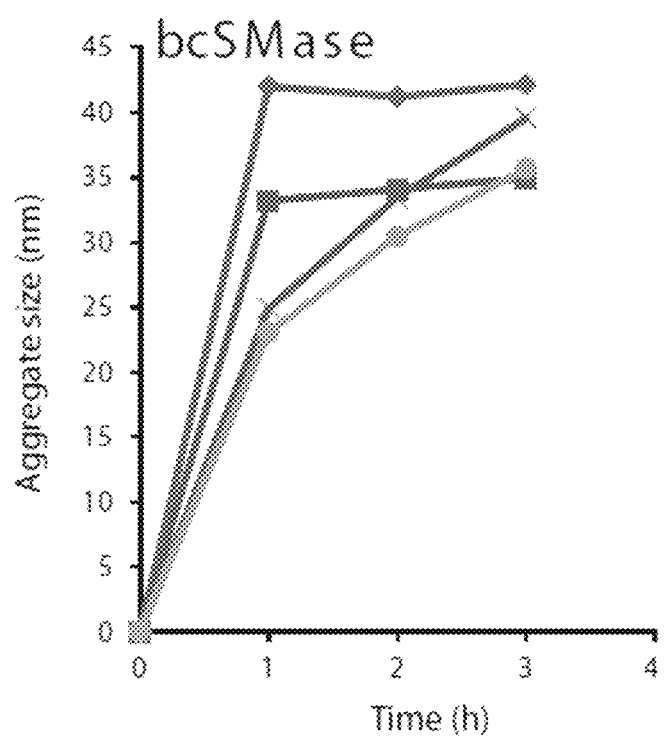
FIG. 1D. Aggregation of LDL induced by phospholipolysis. LDL from four blood donors was incubated with bacterial SMase (bcSMase) for the indicated times. Aggregation was followed by DLS.

SEQ ID NO:1. The amino acid sequence of the *Homo sapiens* SMase.
SEQ ID NO:2. The mRNA sequence of the *Homo sapiens* SMase.

DETAILED DESCRIPTION OF THE DISCLOSURE

The disclosure relates to a method to measure the intrinsic susceptibility of circulating LDL particles to aggregate upon modification. LDL aggregation takes place in human atherosclerotic lesions, such as in coronary artery plaques and in carotid artery plaques. Therefore, LDL aggregation is considered a pathogenic mechanism of human coronary atherosclerosis and human carotid atherosclerosis. Coronary atherosclerosis, again, is the root cause of coronary artery disease and myocardial infarction, and carotid atherosclerosis is a significant cause of ischemic stroke.

The present study focused on the intrinsic susceptibility of circulating LDL particles to aggregate upon modification. Inter-individual differences in this quality were examined. In this study, it was for the first time ever shown that there exist differences in LDL aggregation susceptibility between individuals. A novel, reproducible method to assess the susceptibility of LDL particles to aggregate during lipolysis induced ex vivo by human recombinant secretory sphingomyelinase (hrSMase) was developed. Aggregation-prone LDL contained more sphingolipids and less phosphatidylcholines than did aggregation-resistant LDL. The inventors thus found that the intrinsic susceptibility of LDL to aggregate ex vivo varies considerably between human subjects when assessed by modification with hrSMase. Importantly, the degree of aggregation-susceptibility of LDL predicted future cardiovascular deaths in a cohort of patients with diagnosed ASCVD, independently of conventional risk factors. Therefore, the susceptibility of LDL to aggregate may serve as a novel measurable and, as also shown in this study, a modifiable component of human ASCVD.

The susceptibility of LDL to aggregate is an important factor regarding prognosis, diagnosis and surveillance of ASCVD and cardiometabolic diseases, such as type 2 diabetes and related conditions at various stages of their development. The clinical conditions caused by atherosclerosis of an affected artery include CAD due to atherosclerosis in coronary arteries, carotid artery disease due to atherosclerosis in carotid arteries, peripheral artery disease due to atherosclerosis of the large arteries of the lower limbs, atherosclerotic aneurysm of the abdominal aorta due to atherosclerosis in the abdominal aorta, ischemic stroke due to atherosclerosis in large intracranial arteries, and renovascular hypertension caused by renal artery stenosis due to atherosclerosis in renal arteries. The acute clinical complications of the above-mentioned atherosclerotic arterial diseases include local occlusive and distal embolic atherothrombotic conditions. The acute clinical complications of coronary artery disease include acute coronary syndromes with or without ensuing non-fatal or fatal myocardial infarction, and sudden cardiac death. The acute clinical complications of carotid artery disease include TIA (transient ischemic attack) and ischemic stroke. The acute clinical complication of atherosclerotic aortic aneurysm is rupture of the aneurysm. The clinical presentation of peripheral arterial disease is claudication, and ultimately gangrene and amputation of a leg. Patients with carotid artery disease or peripheral arterial disease have a strongly increased risk of premature coronary death, which reflects the facts that patients with carotid ASCVD or peripheral ASCVD also have coronary atherosclerosis, and that coronary ASCVD is the most fatal disease of the three. Patients at increased risk of atherosclerotic cardiovascular disease may have comorbidity, such as rheumatoid arthritis, obesity, metabolic syndrome and/or type 2 diabetes.

LDL (low-density lipoprotein) as used herein refers to one of the five major groups of lipoproteins which transport fat molecules around the body in the circulating blood and in the extracellular fluid. These five major lipoprotein groups (compared to surrounding water) are from the least dense (the largest particles) to the most dense (the smallest particles) the following ones: chylomicrons (aka ULDL by the overall density naming convention), very low-density lipoprotein (VLDL), intermediate-density lipoprotein (IDL), low-density lipoprotein (LDL) and high-density lipoprotein (HDL). All lipoproteins carry in their core compartment water insoluble neutral lipids which are triglycerides and cholesteryl esters. Chylomicrons and VLDL particles carry triglycerides derived from intestine and liver, respectively, and they deliver the triglycerides to fat cells for storage and to muscle cells for energy. LDL particles carry liver-derived cholesteryl esters to all cells. HDL particles, again, remove cholesterol from cells and carry it back to the liver. A fraction of circulating LDL particles ends up in the arterial wall, where the particles become oxidized or enzymatically modified locally in the arterial wall. Such modified LDL particles deliver their cholesteryl esters to the cells in the arterial wall, notably macrophages, which become filled with the cholesteryl esters. Such, cholesteryl ester-filled macrophages in the arterial wall are called foam cells, and they are the hallmark of atherosclerosis. Modified LDL particles also fuel inflammatory reactions in the arterial wall. Cholesterol accumulation and inflammation drive the initiation and progression of atherosclerosis.

The blood plasma level of LDL is determined by measuring the level of LDL cholesterol (LCL-C), and the blood plasma level of HDL is determined by measuring the level of HDL cholesterol (HDL-C). Case-control and prospective epidemiological studies have shown direct correlations between ASCVD and serum levels of total cholesterol (cholesterol carried in all lipoprotein particles) and between ASCVD and the cholesterol carried in LDL particles, i.e. the LDL-C, and an inverse correlation between ASCVD and HDL-C levels.

The LDL aggregation as used herein refers to a group of LDL particles that form aggregates, which are composed of individual LDL particles bound to each other. Originally, LDL aggregation has been demonstrated to occur when LDL particles in suspension are vigorously shaken, a method called "vortexing". LDL aggregates may also contain lipid droplets and lipid vesicles, which are formed when individual LDL particles fuse together and form larger particles. Different treatments of LDL particles in vitro, involving proteolysis, lipolysis or oxidation of the particles have been used to induce LDL fusion in vitro. The LDL instability or LDL aggregation susceptibility can be used as a metric of the susceptibility of plasma LDL particles to aggregate.

There are two major and three minor phospholipids in human plasma, the major ones being phosphatidylcholine and sphingomyelin, and the minor ones being phosphatidylinositol, phosphatidylethanolamine and lysophosphatidylcholine. Up to 18% of total phospholipids in human blood plasma is composed of sphingomyelin. In the blood plasma, sphingomyelin (SM) is a component of various lipoprotein particles. In all tissues SM is also a component of various cell membranes, both the surface cell membrane and the membranes of various subcellular organelles. Term sphingomyelin or SM is found especially in the membranous myelin sheaths that surround some nerve cell axons, which usually also contain phosphocholine and ceramide, or a phosphoethanolamine head group. Therefore, sphingomyelins can also be classified as sphingophospholipids. Together with free cholesterol and phosphatidylcholine (PC), SM forms a phospholipid monolayer at the surface of plasma lipoproteins, and the ratio of SM/PC varies widely among various lipoproteins. Animal studies have shown that plasma SM levels are closely related to the development of atherosclerosis. Plasma lipoprotein SM content may be important in atherogenesis because the ratio of SM to PC is increased 5-fold in VLDL from hypercholesterolemic rabbits.

Aggregated LDL has been suggested to promote atherogenesis by inducing lipid accumulation in the arterial wall both extra- and intracellularly. A major trigger for aggregation of LDL particles within the arterial wall is their digestion by the secretory sphingomyelinase (SMase), and genetic deletion of this enzyme in hypercholesterolemic animals dramatically retards atherosclerotic plaque development. The importance of SMase in human atherogenesis is reflected by the observation that large LDL aggregates isolated from human atherosclerotic lesions are enriched in ceramides, the lipolytic products of SMase action.

In the present study, to induce aggregation, LDL was first treated with the SMase. SM carried into the arterial wall on atherogenic lipoproteins may be locally hydrolyzed by the SMase synthesized and secreted by the cells in the arterial wall, thereby promoting lipoprotein aggregation and macrophage foam cell formation. The term sphingomyelinase or SMase or sphingomyelin phosphodiesterase or acid sphingomyelinase as used herein refers to a hydrolase enzyme that is involved in sphingolipid metabolism reactions and is active in acidic conditions. SMase is a member of the DNase I superfamily of enzymes and is responsible for breaking SM down into phosphocholine and ceramide. The activation of SMase has been suggested as a major route for the production of ceramide in response to cellular stresses. The sphingomyelinase is preferably recombinant. More preferably, the recombinant sphingomyelinase is mammalian or eukaryotic sphingomyelinase. Most preferably, LDL is treated with hrSMase. The human recombinant sphingomyelinase is unique in its ability to induce aggregation of LDL particles in vitro under acidic conditions. Also bacterial SMase (bcSMase) can be used that is able to function at acidic conditions. SMase sequence can for example be as presented in sequences with ID numbers SEQ ID NO:1 or SEQ ID NO:2. In addition, the SMase can be any fragment or variant of such SMases.

The recombinant protein or recombinant polypeptide as used herein refers to a polypeptide or protein produced by a host organism through the expression of a recombinant nucleic acid molecule, which has been introduced into said host organism or an ancestor thereof, and which comprises a sequence encoding said polypeptide or protein. The human recombinant enzyme used in this study acts optimally at acidic pH. Generation of large (>200 nm) LDL aggregates takes place optimally at acidic pH, such as found in the extracellular fluid of human coronary and carotid atherosclerotic lesions.

In the present study, the treatment with sphingomyelinase is performed at pH 3-7. More preferably, the pH of said enzymatic reaction is between 4 and 6.5. pH can be between 5 and 6. More precisely, pH can be selected to be 5.0, 5.1, 5.2, 5.3, 5.4, 5.5, 5.6, 5.7, 5.8, 5.9, and 6.0. Even more preferably, said enzymatic reaction is performed between 5 and 5.5. Most preferably, the treatment is performed at pH 5.5. The enzyme treatment time is between 1 to 48 h. Preferably, the treatment time is 1 to 8 hours. A treatment time of 10 minutes to 2 hours can be used. Treatment time can also be 10, 15, 30 or 60 minutes. Also treatment times of 1 hour, 2 hours, 3 hours, 4 hours and 5 hours can be used. Most preferably the treatment time is 2 hours. The enzyme treatment can be performed at 30-40° C. in a buffer or more precisely at 30, 31, 32, 33, 34, 35, 36, 37, 38, 39 or 40° C. in a buffer. Preferably, the enzyme treatment is performed at 37° C. The concentration of hrSMase is standardized by its enzymatic activity towards LDL-SM so that the enzyme is used in a concentration (for example 1 mU/ml) that is able to induce at least 80 hydrolysis of LDL-SM within 1 h incubation at pH 5.5. The incubation can be performed in the presence of 20-200 µmol/l of $Zn^{2+}$. Preferably, the concentration of $Zn^{2+}$ is 50 µM.

The LDL aggregates are detected as an increase in the size of the forming aggregates. The dynamics of the formation of LDL aggregates is followed preferably by dynamic light scattering (DLS) or by a method utilizing absorbance measurements, such as UV-vis absorbance spectroscopy.

The predetermined value for an analyte in a sample refers to the base or threshold concentration of an analyte in a sample in normal individuals; and if the value of the analyte in said sample is above such predetermined value, the test result is positive. The predetermined value for an analyte in a sample may vary depending on the format of the assay, and the specific reagents employed in the assay, but can be determined and set by those skilled in the art by assessing the concentration of the analyte in a sample in normal individuals relative to control samples containing known amounts of the analyte.

The sample used for detecting or determining the amount or level of LDL aggregation can be a group of isolated/separated LDL particles, serum, plasma or whole blood. Preferably the sample is a serum sample. In the present procedure, the predetermined values of LDL are set so that the LDL concentration, as determined by the protein concentration or apolipoprotein B-100 concentration of LDL, in a sample is 0.05-5 mg/ml. More preferably, the concentration is 0.2 mg/ml. The LDL concentrations are set to be the same in all samples that are compared. The concentration of LDL-cholesterol in a serum sample can range from 1 to 10 mmol/L (40 to 400 mg/dL).

One aspect of the present description is detecting LDL aggregates in a sample and comparing the sizes of LDL aggregates detected with respective predetermined values of LDL aggregate sizes, wherein the detection of elevated sizes of LDL aggregates is indicative of the presence of atherosclerotic cardiovascular diseases or cardiometabolic diseases or indicative of the risk of atherosclerotic cardiovascular diseases or cardiometabolic diseases. The detected sizes of LDL aggregates are elevated when the size of LDL aggregates is above the predetermined value for LDL aggregates. The diameters of LDL aggregates can be of sizes from 100 nm to 8000 nm. The diameters or sizes of the aggregates can be 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900 and 8000 nm. Generally, the aggregate is considered large when its diameter is at least 200 nm. Preferably, the aggregate size to be detected is between 20 nm and 2000 nm. Aggregation prone LDL refers to LDL that forms aggregates having diameters of at least 500 nm in 2 h upon enzyme treatment.

The terms positive and negative refer to the size of LDL aggregates to be above (high or positive) and below (low or negative) a predetermined value (baseline, threshold or reference size), respectively.

In most studies examining the relationship between lipid markers and ASCVD risk, the lipid composition of whole plasma, rather than that of circulating LDL particles, has been determined. In such studies, high levels of plasma SM and low levels of certain LPC-species were associated with increased risk for future development of clinically significant ASCVD. In addition, plasma levels of certain ceramide species have recently been found to predict future risk of cardiovascular death in patients with ASCVD. These results from whole plasma reflect the lipid composition of all plasma lipoprotein classes. Therefore, the present findings demonstrating that aggregation-prone LDL particles are SM-rich, ceramide-rich, PC-poor, and LPC-poor may explain the previously reported associations between plasma levels of these lipids and future ASCVD risk. Moreover, the present work supports a mechanistic chain from these compositional differences to differences in LDL quality that predispose it to SMase-induced aggregation, to plaque initiation, progression, and, ultimately to destabilization. In the present study, it was found that the susceptibility of LDL to aggregate is an important factor regarding prognosis, diagnosis and surveillance of atherosclerotic cardiovascular diseases. It is suggested that the susceptibility of LDL to aggregate could also be an important factor regarding cardiometabolic diseases, such as type 2 diabetes and related conditions at various stages of their development, in which plasma levels of certain ceramide species have been found to be of prognostic value.

The present inventors have found that interventions in animal models to rationally alter LDL composition lowered its susceptibility to aggregate and slowed the development of atherosclerosis in the animals. Similar compositional changes induced in humans by Proprotein convertase subtilisin/kexin type 9 (PCSK9) inhibition or healthy diet also lowered LDL aggregation susceptibility.

In this study, it is shown that the susceptibility of LDL particles to aggregate in the presence of hrSMase varies significantly amongst human subjects and depends on the lipid composition of the LDL particles isolated from their blood. The presence of aggregation-prone LDL was associated with future CAD deaths independently of conventional CAD risk factors including plasma LDL-C concentration, smoking and hypertension. Importantly, it is now shown that the susceptibility of LDL particles to aggregate can be favourably modified in humans by nutritional and medical interventions and in vivo by altering LDL lipid composition. The data that is presented in more detail in the Examples indicates that aggregation-prone human LDL particles are enriched in SM and ceramides and contain less choline phospholipids (PC and LPC) and less TGs than aggregation-resistant LDL particles. Causality of these lipids in LDL aggregation susceptibility was established by altering their contents in isolated LDL in vitro, in humans by diet and by PCSK9 inhibition, and in three atherosclerotic mouse models in vivo. Increase in dietary vitamin E was associated with decreased LDL aggregation, and, when the aggregation data were normalised for changes in the consumption of dietary vitamin E, increased intake of sucrose was found to associate with accelerated aggregation. Interestingly, plasma levels of SM are strongly controlled by genetic effects. This could partly explain the observation that the aggregation susceptibility decreased in only two thirds of the subjects in the healthy diet group. Similarly, inhibition of PCSK9 decreased LDL aggregation in two thirds of the subjects. Thus, the measurement of altered LDL aggregation susceptibility—due to for example cholesterol lowering medication or healthy diet—could be useful in monitoring the disease state of a person or in predicting a risk for future atherosclerotic cardiovascular diseases or potentially cardiometabolic diseases.

The term cholesterol lowering medication as used herein refers to various medications that are used to lower blood cholesterol levels. Statins—also known as HMG CoA reductase inhibitors—are recommended for most patients with an increased risk of ASCVD, because they're the most studied cholesterol-lowering drug class that has been directly associated with reducing the risk of a heart attack or stroke. The currently available statins are atorvastatin (Lipitor®), rosuvastatin, fluvastatin, lovastatin, pravastatin, simvastatin, and pitavastatin. Selective cholesterol absorption inhibitors are a relatively new class of cholesterol-lowering medications that work by preventing cholesterol from being absorbed in the intestine. Selective cholesterol absorption inhibitors are most effective at lowering LDL cholesterol. They may also have modest effects on lowering TGs (blood fats) and raising HDL cholesterol. Still another class of cholesterol lowering medication are bile acid-binding resins that work in the intestines by promoting increased disposal of cholesterol from the body. Human body uses cholesterol to make bile acids, which are necessary for the digestion of dietary fats. As the resins bind bile acids, the bile acids cannot be used during digestion. The liver responds by making more bile acids from cholesterol. As a response the liver cells increase the number of LDL receptors on their surfaces, and thereby take up more LDL particles from the circulation. This, again results in lowering of the concentration of LDL particles in the circulation, which can be measured as lowering of plasma LDL-C concentration. The subjects of the method disclosed by this description may have cholesterol lowering medication. These include: (1) the HMG CoA reductase inhibitors or statins, [for example atorvastatin (Lipitor), fluvastatin (Lescol), lovastatin (Mevacor, Altoprev), pravastatin (Pravachol), rosuvastatin (Crestor), simvastatin (Zocor), pitavastatin (Livalo)]; (2) selective cholesterol absorption inhibitors [ezetimibe (Zetia)]; (3), statin/ezetimibe combinations [atorvastatin/ezetimibe (Liptruzet) and simvastatin/ezetimibe (Vytorin)]; (4) bile acid-binding resins [cholestyramine (Questran), colestipol (Colestid), and colesevelam (Welchol); (5) fibric acid derivatives or fibrates [gemfibrozil (Lopid) and fenofibrate (Lipofen)]; (6) proprotein convertase subtilisin/kexin type 9 (PCSK9) inhibitors [such as the monoclonal antibodies evolocumab (Repatha) and alirocumab (Praluent)], and inclisiran, a small interfering RNA leading to degradation of PCSK9 mRNA transcripts (Phase III study going on)]; (7) inhibition of hepatic apolipoprotein B synthesis with an antisense oligonucleotide [mipomersen (Kynamro)]; and (8) the small-molecular inhibitor of hepatic microsomal triglyceride transfer protein [lomitapide (Juxtapid)]. The cholesterol lowering method can be selected, in addition to the cholesterol-lowering drugs, for example from the group consisting of a healthy diet, such as a Healthy Nordic Diet or Mediterranean Diet, or a low sucrose diet, or a diet low in saturated fats. In addition, cholesterol-lowering supplements, such as plant stanols, plant steros, and fish oil products, can be used. The term "plant stanols" and "stanols" as used herein mean naturally occurring substances that are hydrogenated compounds of the respective plant sterols, typically by an addition of two hydrogen atoms. Plant stanols generally are saturated plant sterols, such as β-sitostanol, campestanol and stigmastanol.

The term "plant stanol esters" as used herein mean fatty acid or other esters of plant stanols. Plant stanols, and esters thereof, are described in Cater N. B., "Plant Stanol Ester: Review of Cholesterol-Lowering Efficacy and Implications for Coronary Heart Disease Risk Reduction," Preventative Cardiology 2000; 3, 121-130. Plant stanol esters may be prepared, for example, by esterifying a mixture of plant stanols derived from one or more edible oils or by-products of the kraft paper pulping process with fatty acids, which are preferably food-grade. A plant stanol ester mixture preferably contains a combined weight of at least about 80 percent sitostanol and campestanol. Plant stanol esters may be measured by the following known methods, which were developed by McNeil Consumer Healthcare dated Feb. 15, 2000: (1) "Determination of Stanols and Sterols in Benecol Tub Spread;" (2) "Determination of Stanols and Sterols in Benecol Dressing;" (3) "Determination of Stanols and Sterols in Benecol Snack Bars;" or (4) "Determination of Stanols and Sterols in Benecol Softgels." Non-limiting examples of foods comprising plant stanol esters includes those sold by Benecol.

An object of the present disclosure is a method for determining the susceptibility of LDL particles to form aggregates, said method comprising the steps of treating LDL particles with sphingomyelinase enzyme at acidic pH in a sample, detecting formation of LDL aggregates in said sample and comparing the sizes of LDL aggregates detected with respective predetermined values of LDL aggregates, wherein the detection of elevated sizes of LDL aggregates as compared to the predetermined values of LDL aggregates is indicative of the presence or risk for an atherosclerotic cardiovascular disease or a cardiometabolic disease. Another object is the method, wherein determining the susceptibility of LDL particles to form aggregates means detecting the susceptibility of LDL particles to form large aggregates. The predetermined value of LDL aggregate size can be for example 200 nm, 300 nm, 400 nm or 500 nm. Sizes of LDL aggregates are thus in each case considered elevated when the aggregates' diameters are at least 200 nm, 300 nm, 400 nm or 500 nm. The sample is considered to contain aggregates of elevated size, when the median size of said aggregates is larger than the predetermined value.

In one embodiment the sphingomyelinase treatment is performed for 1 to 8 h. In another embodiment the sphingomyelinase treatment is performed for 2 h. In one embodiment the enzyme treatment is performed in the presence of 50-100 μM of $Zn^{2+}$.

In one object of the disclosure, the sphingomyelinase is selected from a group consisting of mammalian, eukaryotic, and bacterial sphingomyelinase. More preferably, the sphingomyelinase enzyme is a recombinant enzyme. Most preferably, the sphingomyelinase enzyme is a recombinant human enzyme.

In one object of the disclosure, detecting formation of LDL aggregates in a sample is done by dynamic light scattering.

In one embodiment, the enzyme treatment is done performed at pH 4-6.5. More preferably, the enzyme treatment is done performed at pH 5-5.5.

According to one embodiment, the method is used for estimating the need for cholesterol-lowering medication. According another embodiment said method is used for monitoring the effect of therapy on atherosclerotic cardiovascular disease or cardiometabolic disease.

According to one object, the sample comprises isolated LDL particles, serum, plasma or whole blood. Most preferably, the sample is a serum sample.

The description also discloses a method for constructing a risk prediction model for the presence of an atherosclerotic cardiovascular disease or a cardiometabolic disease or risk of an atherosclerotic cardiovascular disease or a cardiometabolic disease, wherein said method is based on detection of increased sizes of LDL aggregates in a sample.

The description further discloses a kit for determining the susceptibility of LDL particles to form aggregates, containing at least the following two types of reagent composition:

(i) a sphingomyelinase enzyme reagent for producing modified LDL particles;

(ii) a reagent composition for measurement of LDL aggregates, comprising microplates with sphingomyelinase and buffer, such as 20 mM MES buffer, pH 5.5, containing 150 mM NaCl and 50 µM $ZnCl_2$. The kit may also include other additives.

Taken the present results together, it seems that one of the unknown endogenous risk factors not included in the currently available risk estimation tools for the estimation of a person's cardiovascular risk is the intrinsic susceptibility of LDL to aggregate ex vivo. LDL aggregation susceptibility as a risk factor for atherosclerotic cardiovascular diseases or cardiometabolic diseases is a novel concept conceived in the present study and measuring LDL aggregation is a novel method developed by the present inventors. The present data implicate LDL aggregation as an important factor in arterial lipid accumulation, atherosclerotic plaque inflammation, and even plaque rupture. Therefore, as a novel component of precision medicine in the cardiovascular field, determination of LDL aggregation could provide critical incremental information to the systematic cardiovascular risk estimation of a person at risk. In a Finnish cohort of cardiovascular patients, the present inventors identified LDL aggregation as a parameter associating with cardiovascular deaths. The aggregation-prone LDL was found to predict death from cardiovascular causes independent of conventional atherosclerosis risk factors. Importantly, prior and current data indicate that aggregated LDL has the potential to promote multiple steps along the atherogenic pathway from LDL retention to maladaptive responses that include initiation and growth of atherosclerotic lesions, plaque destabilization, and plaque rupture. Any treatment that induces a favourable change in LDL lipid composition offers a mean to attenuate LDL aggregation within the arterial wall and its deleterious consequences. These results emphasize the importance of LDL quality in human atherosclerotic cardiovascular disease. Moreover, measurement of the susceptibility of LDL to aggregate may serve as a predictive biomarker for the identification of patients at significant residual or unrecognized risk of cardiovascular death and those who might benefit from personalized, targeted interventions.

EXAMPLES

Human Plasma

Human blood plasma samples were obtained from healthy volunteers (Finnish Red Cross Blood Service, Helsinki, Finland), 100 samples derived from subjects participating in the Health 2000 Health Examination Survey, 48 samples from Corogene survey (1), 57 samples from SYSDIET (Systems biology in controlled dietary interventions and cohort studies) survey (2,3), 29 samples from 18-week diet group and 28 samples from the 24-week diet group, and 40 samples from EQUATOR study (4).

The use of human material conforms to the principles outlined in the Declaration of Helsinki, and the studies were approved by the Ethics Committee of Helsinki University Central Hospital (Helsinki, Finland) and the Ethical Committee of the Hospital District of Northern Savo. Written informed consent was obtained from all patients.

Isolation of LDL, Lipid and Lipoprotein Measurements
Lipid Measurements

Fasting plasma total cholesterol and triglycerides were enzymatically measured (Roche Diagnostics, GmbH, Mannheim, Germany). ApoB-100 content was measured with ELISA-kit (MABTECH, Nacka, Sweden).

LDL Isolation

LDL (d=1.019 to 1.063 g/ml) was isolated from plasma by KBr-based sequential ultracentrifugation as described before (5). LDL concentrations are expressed as their protein concentration, which were determined by the BCA method using bovine serum albumin as a standard, or, as apoB-100 concentration determined by ELISA.

Measurement of LDL Aggregation

Development of a Method to Quantify Person-to-Person Variability in LDL Aggregation-Susceptibility Firstly, inter-individual variability in LDL aggregation using agents that have been reported to cause LDL aggregation was tested. LDL aggregation was induced at LDL concentration of 0.5 mg/ml by oxidation (incubation with 5 µM $CuSO_4$), by proteolysis (incubation with 0.1 mg/ml α-chymotrypsin from bovine pancreas (Sigma-Aldrich)), or by lipolysis (incubation with 50 mU/ml phospholipase A2 ($PLA_2$) from bee venom (Sigma-Aldrich)), with 200 mU/ml SMase from *Bacillus cereus* (bcSMase, Sigma-Aldrich)), or with 75 µg/ml hrSMase (a kind gift from Genzyme or produced in house). The incubation buffer was 20 mM Tris-HCl, pH 7.4, containing 150 mM NaCl and 2 mM $CaCl_2$ and 2 mM $MgCl_2$, except in the case of hrSMase, where the incubation buffer was 20 mM MES, pH 5.5, containing 150 mM NaCl and 50 µM $ZnCl_2$. LDL size was determined at the beginning of the incubation and aggregate size was determined at the indicated time points by dynamic light scattering (DLS) (Zetasizer Nano, Malvern Instruments, Malvern Works, UK or Wyatt DynaPro Plate Reader 11, Wyatt Technology, California, USA).

Figure 1E:
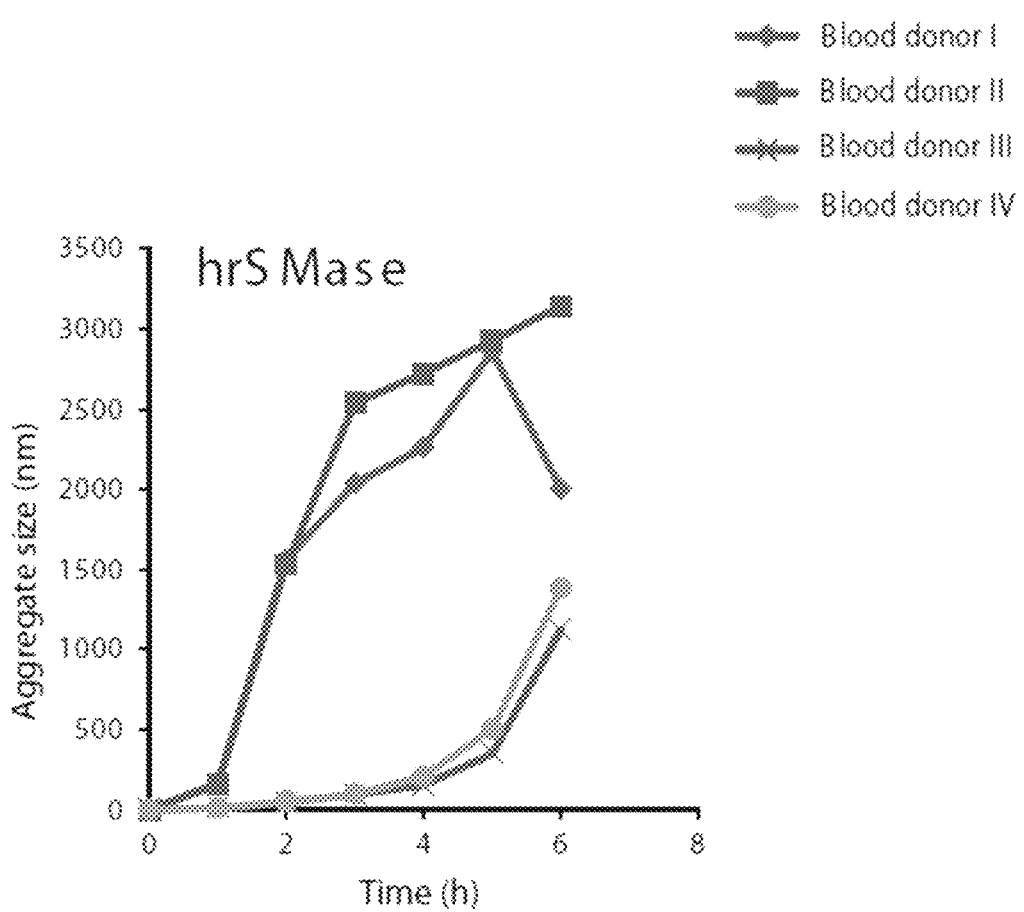
FIG. 1E. Aggregation of LDL induced by phospholipolysis. LDL from four blood donors was incubated with human recombinant SMase (hrSMase) for the indicated times. Aggregation was followed by DLS. Notice the difference in y-axis scales between panels in FIG. 1A-E.

FIGS. 1a-d confirms that oxidation, proteolysis, and lipolysis by $PLA_2$ and bcSMase each caused aggregation of LDL. The extent of aggregation of LDL from four representative fasting human donors was essentially identical, indicating that these assays are uninformative about possible variations in LDL quality. In contrast, FIG. 1e shows large differences in aggregation of the same LDL samples when incubated in the presence of hrSMase at pH 5.5. Moreover, the extent of LDL aggregation was far greater than with any of the other agents (compare y-axis scales). Therefore, hrSMase-treatment at acidic pH was chosen for systematic analysis of inter-individual differences in the susceptibility of LDL to aggregation.

Figure 2A:
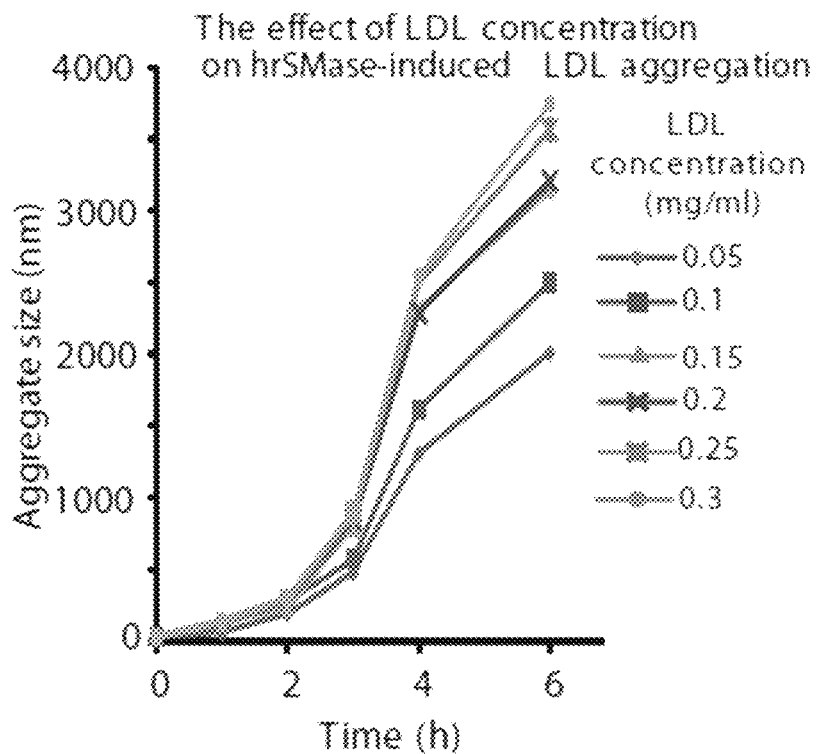
FIG. 2A. Validation of LDL aggregation analysis. LDL aggregation was induced by hrSMase and aggregation was followed by DLS. LDL was treated with 75 µg/ml of hrSMase at the indicated LDL concentrations.
Figure 2B:
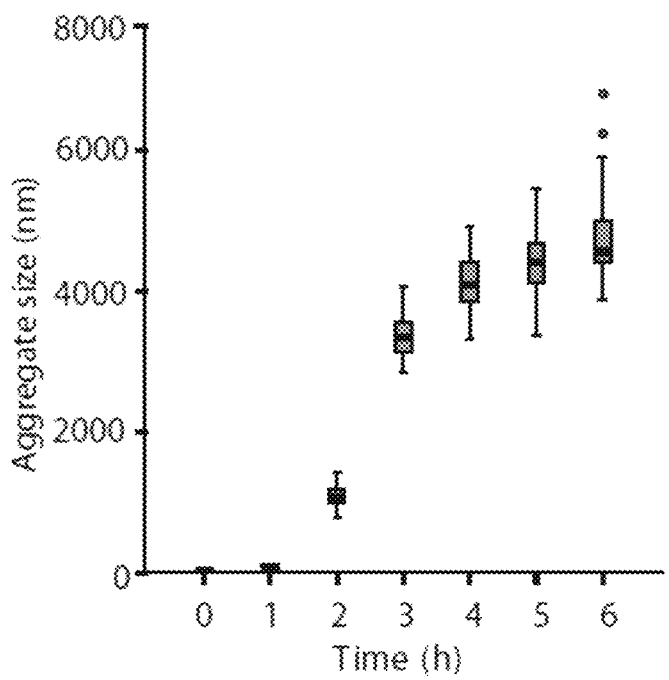
FIG. 2B. Validation of LDL aggregation analysis. To determine the inter-assay variation in LDL aggregation, one plasma sample was divided into 26 aliquots, and LDL was separately isolated and LDL aggregation determined by DLS. The box plot diagram shows the variation in the sizes of LDL aggregates at the various time points.
Figure 2C:
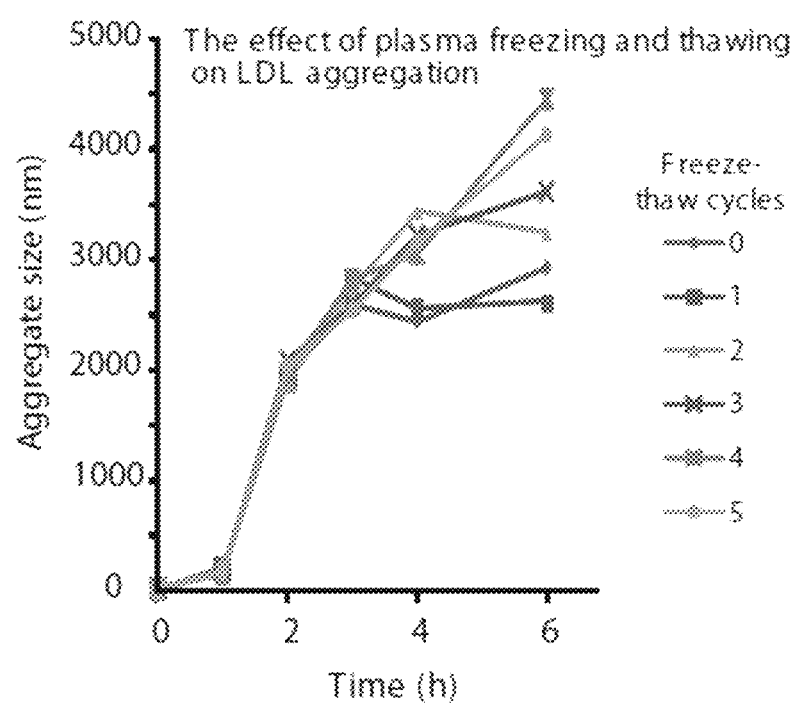
FIG. 2C. Validation of LDL aggregation analysis. One plasma sample was subjected to 0-5 freeze-thaw cycles as indicated, LDL was isolated and LDL aggregation determined by DLS.

Several approaches were used to standardize the method. First, it was found that hrSMase-induced aggregation of a single preparation of LDL was affected by the starting concentration of LDL. LDL aggregation was assayed at LDL concentrations of 0.05, 0.1, 0.15, 0.2, 0.25 and 0.3 mg/ml after aggregation was induced with hrSMase. The particle size was followed with DLS for up to 6 hours (FIG. 2a) and concentration 0.2 mg/ml was chosen for standard assay. Second, the concentration of hrSMase was standardized by its enzymatic activity towards LDL-SM and used a concentration of the enzyme (75 µg/ml) that was able to induce nearly complete hydrolysis (>80%) of LDL-SM within a 1 h incubation at pH 5.5. To define inter-assay variance, LDL was separately isolated from one plasma sample that was divided into 26 aliquots and stored at −80° C. The aggregation susceptibility of LDL was determined separately from these samples (FIG. 2b). In preparation for analysis of biobanked plasma samples held at −80° C., it was found that hrSMase-induced aggregation was unaffected by one freeze-thaw cycle and at most moderately affected by up to five freeze-thaw cycles (FIG. 2c).

In the standard assay, LDL isolated from human plasma was extensively dialyzed against 20 mM MES buffer, pH 5.5, containing 150 mM NaCl and 50 µM $ZnCl_2$ and its apoB-100 concentration was determined by ELISA (Mabtech). The sample was diluted with the same buffer to give a final concentration of 0.2 mg of apoB-100/ml and 75 µg/ml of hrSMase was added to LDL. The size of LDL was determined immediately and once every hour for up to 6-hours. An aliquot was taken at the same time points for phosphorylcholine measurement. The degree of SM hydrolysis was determined by measuring the amount of phosphorylcholine from the samples with Amplex Red reagent (Invitrogen).

SM- PC-, and LPC-Enrichment of LDL Ex Vivo

To exchange LDL surface phospholipids, LDL (2 mg/ml) was incubated with phospholipid vesicles (1 mM phosphatidylcholine 18:1/16:0 (1-palmityl-2-oleyl-sn-glycero-3-phosphocholine), lysophosphatidylcholine 16:0 (1-Palmitoyl-2-Hydroxy-sn-Glycero-3-Phosphocoline) or sphingomyelin 16:0 (N-Palmitoyl-D-erythro-sphingosylphosphorylcholine) each from Avanti Polar Lipids) overnight at 37° C. in buffer A (5 mM Tris, 150 mM NaCl, 1 mM EDTA, pH 7.4). The vesicles had been prepared by sonicating 10 mM lipid solutions using a Branson Sonifier 250 sonicator (6 times for 5 minutes) in buffer A. Vesicles were removed with sequential ultracentrifugation (d<1.019 g/ml KBr) repeated twice.

Lipid Mass Spectrometry Analyses

The lipid compositions of the SYSDIET-study LDL, the in vitro-manipulated human LDL and the myriocin mouse model LDL samples were determined by Agilent 6490 Triple Quad LC/MS with iFunnel technology (Agilent Technologies, California, USA) at the Helsinki University Lipidomics Unit. For the mass spectrometry, the total lipids were extracted from the LDL samples (6) and the extract was evaporated under nitrogen stream and immediatedly solved in choloform/methanol (1:2, v/v). The samples were spiked with a cocktail of several quantitative standards and 1% (v/v) of $NH_3$ was added into the samples just before the analysis to support ionization and prevent adduct formation. Lipids with choline head group were detected by using the specific scanning mode i.e. as precursors of the ion m/z 184. The mass spectra were recorded with MassHunter (Agilent Technologies) software and the quantitative analysis was performed by LIMSA (7) software, which employed the standards and a lipid library. The acyl chain assemblies in each lipid species were studied by recording negative ion mode product ion scans of the anion fragments for all common fatty acids (8). For choline lipids, which do not ionize in negative mode as such, formate adducts served as mother ions, and yielded the anionic fragments of the acyl chains (9).

For Corogene and Health 2000 Health Examination Survey the LDL lipid composition was determined with 5500 QTRAP (SCIEX, Framingham, Mass.) mass spectrometer equipped with Eksigent 100-XL UHPLC system at Zora Biosciences (Espoo, Finland). Lipids were extracted with ethyl acetate:isopropanol (2:8, v/v) including protein precipitation solvent and internal standard solution. Just before the analysis 10 mM ammonium acetate in acetonitrile:2-propanol (4:3, v/v) with 0.1% formic acid was added to the samples (10).

Circular Dichroism (CD) Analyses

Samples of control and SM-, PC- and LPC-enriched LDL particles (1 mg/ml) were treated with SMase for 30-min and lipolysis was stopped by 10 mM EDTA. The LDL particles (50 µg/ml) were analyzed by CD as described previously (11,12).

Mathematical Modeling and Statistical Analyses

Mathematical Analyses of LDL Aggregation Curves to Construct an Aggregation Susceptibility Index For each individual LDL preparation, i, at each time point, t, LDL aggregate size was measured using DLS (at 0, 1, 2, 3, 4, 5, and 6 hours). To estimate the averaged response $y_{i,t}$, the data from all the human studies (Health 2000 (n=100), Corogene (n=48), Sysdiet (n=57)) were modeled with a customized Boltzmann-form of the logistic function using a statistical modeling framework developed and distributed as an open-source R package (CRAN.R-project.org/package=hamlet) as described in (13). Using non-linear mixed-effects modeling, the Boltzmann equation of the logistic function with four population-based fixed parameters ($\alpha$, $\beta$, $\gamma$, and $\delta$) was combined with two terms of individual specific variation ($u_\alpha$, and $u_\delta$) and the error term $\varepsilon_{i,t}$ in equation (1).

$$y_{i,t} = \beta + \frac{\alpha + u_{\alpha,i} - \beta}{1 + e^{\frac{\gamma + u_{\gamma,i} - t}{\delta}}} + \varepsilon_{i,t} \qquad (1)$$

The four population-based-fixed effect parameters ($\alpha$, $\beta$, $\gamma$, and $\delta$) are interpreted as follows:

$\alpha$: the right (top) asymptotical level that is obtained when t→∞ (i.e., theoretical maximal end-point size of the LDL aggregates)

$\beta$: the left (bottom) asymptotical level that is obtained when t→-∞ (related to the original size of the LDL particles)

$\gamma$: the point of inflection, i.e., the center point in time where the sigmoidal curve transitions from concave upwards to concave downwards. Thus, by definition, it is also the time point when the aggregation curve has the steepest upwards slope.

Figure 3A:
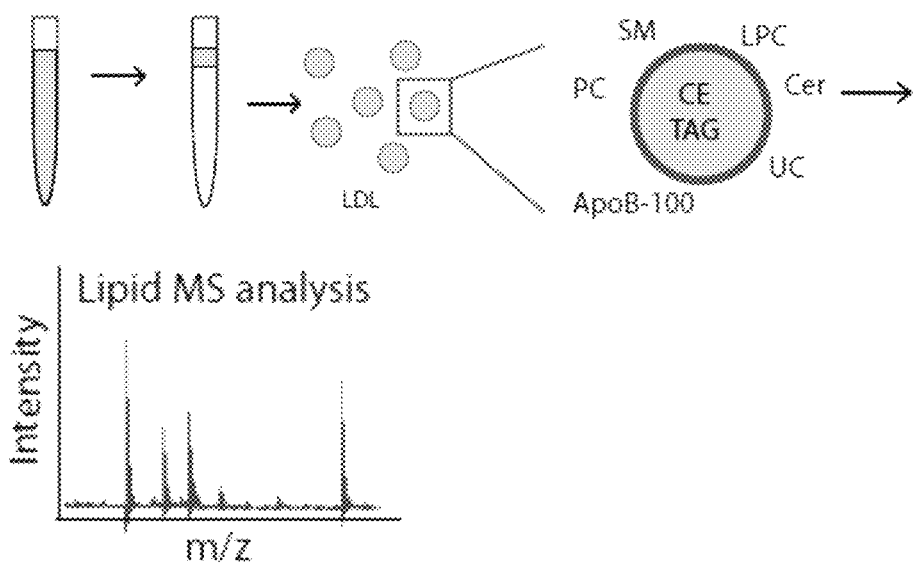
FIG. 3A. The susceptibility of LDL to aggregate strongly correlates with the surface lipid composition of the particles. LDL was isolated from blood plasma and LDL lipidome was analysed using mass spectrometry. PC=phosphatidylcholine, LPC=lysophosphatidylcholine, SM=sphingomyelin, Cer=ceramide.
Figure 3B:
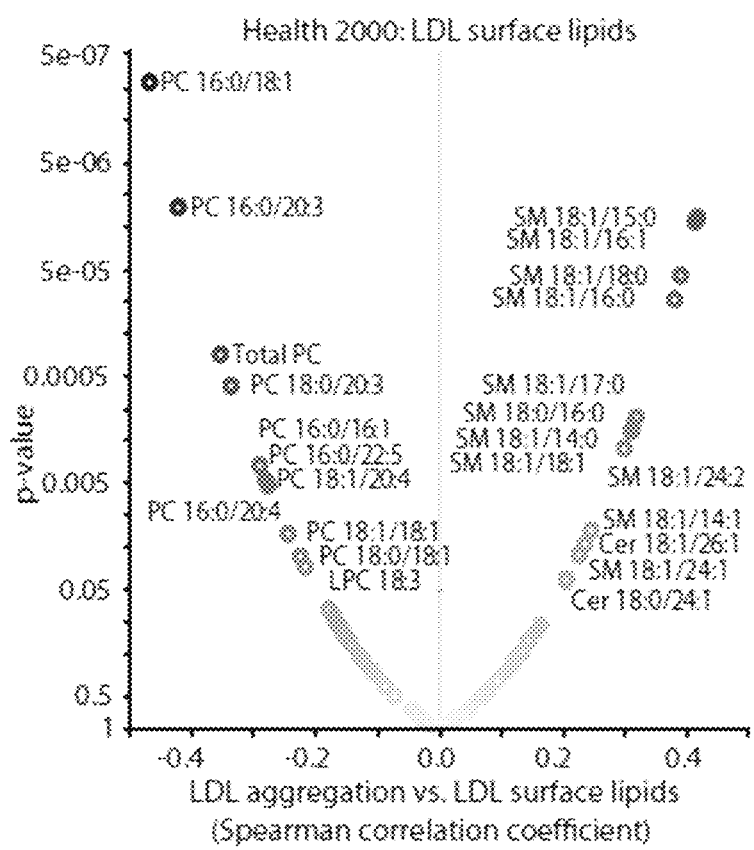
FIG. 3B. The susceptibility of LDL to aggregate strongly correlates with the surface lipid composition of the particles. LDL was isolated from blood plasma and LDL lipidome was analysed using mass spectrometry. Volcano plots showing Spearman correlation coefficients of LDL aggregate size at 2 h vs. LDL surface lipids in Health 2000 samples. Circles to the right of the value 0 indicate positive correlations, and circles to the left of the value 0 indicate negative correlations. The identities of only those lipids with significance correlation values ($p<0.05$) are indicated. PC=phosphatidylcholine, LPC=lysophosphatidylcholine, SM=sphingomyelin, Cer=ceramide.
Figure 3C:
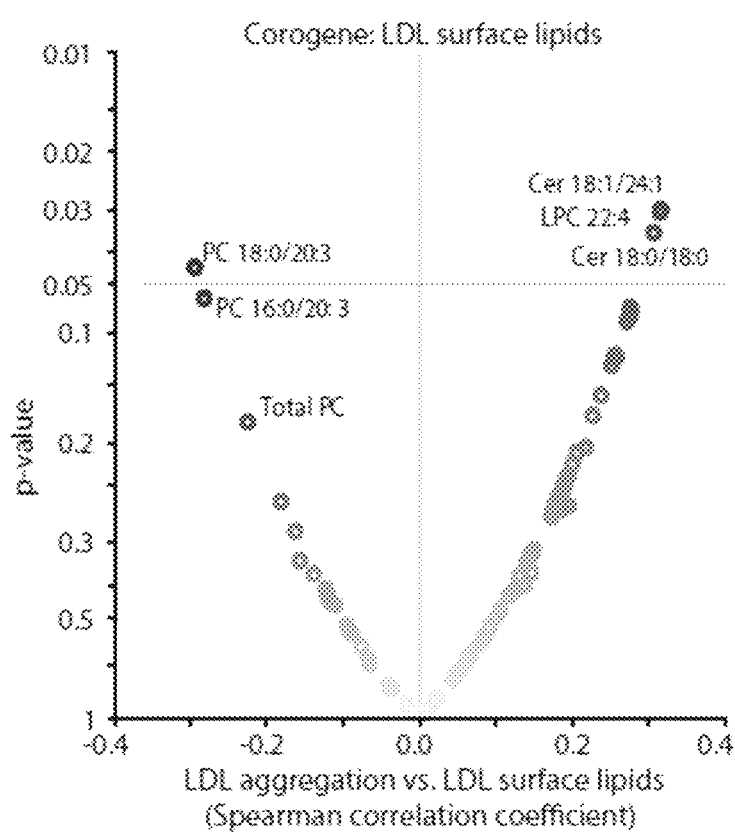
FIG. 3C. The susceptibility of LDL to aggregate strongly correlates with the surface lipid composition of the particles. LDL was isolated from blood plasma and LDL lipidome was analysed using mass spectrometry. Volcano plots showing Spearman correlation coefficients of LDL aggregate size at 2 h vs. LDL surface lipids in Corogene samples. Circles to the right of the value 0 indicate positive correlations, and circles to the left of the value 0 indicate negative correlations. The identities of only those lipids with significance correlation values ($p<0.05$) are indicated. PC=phosphatidylcholine, LPC=lysophosphatidylcholine, SM=sphingomyelin, Cer=ceramide.

$\delta$: the scale parameter that gives the rate of rise (slope) at the point of inflection The terms of individual specific variation are interpreted as follows:

$u_{\alpha,i}$~N(0, $\sigma_\alpha^2$): Individual variation in the asymptotic higher levels specific for each individual i, this model term captures variation in that some curves achieve higher horizontal levels than others as time progresses $u_{\gamma,i}$~N(0, $\sigma_\gamma^2$): Individual variation in the point of inflection specific for each individual i, this model term captures the variation in that some curves start to raise earlier than others as a function of time $\varepsilon_{i,t}$~N(0, $\sigma_e^2$): The normally distributed residual error term specific for each observation FIG. 3a shows the raw data of 100 LDL samples in the Health 2000 cohort (left panel), along with the corresponding model fits (right panel). The fixed effect parameters $\beta$ (related to the original size of the LDL particles) and $\delta$ (reflecting the maximal rate of LDL particle aggregation) did not vary significantly among the 100 samples. The aggregation-resistant samples had a lower $\alpha$ (lower theoretical maximal end-point size), whereas the other samples could not be separated by this parameter. In contrast, $\gamma$, the point of inflection, was able to distinguish the 100 LDL samples according to their aggregation susceptibility. It was further found that LDL aggregate size at 2 h ($y_i$, t=2 h) correlated tightly and significantly with the inflection point ($\gamma$) of the modeled data (FIG. 3b), but not with the theoretical maximal end-point size ($\alpha$). Therefore, the 2-h aggregate size was used to characterize the aggregation-susceptibility of the LDL samples.

Statistical Analyses

The results are presented as average ±SEM or if not normally distributed as medians and interquartile ranges. Statistical significance between groups was determined by Student's t-test when comparing two groups, or by ANOVA or Kruskal-Wallis test followed by post hoc tests. These tests and correlations with two-tailed Spearman correlation were performed using IBM SPSS Software (version 22.0). P values <0.05 were considered to be significant. No experiments or samples were excluded, except for technical failure in the lipidomic analyses of one sample in SYSDIET-study and five samples in Health 2000 Health Examination survey.

The present disclosure discloses a method comprising: providing LDL particles from a human blood plasma or serum sample; mixing the LDL particles with a sphingomyelinase enzyme in a solution at acidic pH; detecting formation of LDL aggregates in the solution, and measuring the size of the detected LDL aggregates.

Further, the present disclosure discloses a method comprising: providing a human plasma or serum sample; mixing the human plasma or serum sample with a sphingomyelinase enzyme at acidic pH; detecting formation of LDL aggregates in the sample, and measuring the size of the detected LDL aggregates.

According to one aspect of the present disclosure, the detected LDL aggregates to have a median size of at least 200 nm.

The present disclosure discloses also a method of treating an atherosclerotic cardiovascular disease or a cardiometabolic disease in a human subject in need thereof, the method comprising administering to the human subject a therapeutically effective amount of a cholesterol lowering medication, wherein LDL particles from a blood plasma or serum sample of the human subject upon treatment with sphingomyelinase enzyme at acidic pH has been determined to form LDL aggregates that have a median size of at least 200 nm.

The present disclosure further discloses a method of treating an atherosclerotic cardiovascular disease or a condition associated with LDL aggregation in a human subject in need thereof, the method comprising administering to the human subject a therapeutically effective amount of a cholesterol lowering medication, wherein LDL particles from a blood plasma or serum sample of the human subject upon treatment with sphingomyelinase enzyme at acidic pH has been determined to form LDL aggregates that have a median size of at least 200 nm.

One aspect of the present disclosure is a method of treatment comprising: providing LDL particles from a human blood plasma sample of a human subject; mixing the LDL particles with sphingomyelinase enzyme in a solution at acidic pH; detecting formation of LDL aggregates in said solution; measuring the size of the detected LDL aggregates, and administering to the human subject a therapeutically effective amount of a cholesterol lowering medication.

The present disclosure discloses a method comprising: providing a human serum sample; mixing the human serum sample with a sphingomyelinase enzyme at acidic pH; detecting formation of LDL aggregates in the sample, measuring the size of the detected LDL aggregates, and administering to the human subject a therapeutically effective amount of a cholesterol lowering medication.

According to one aspect of the disclosure the detected LDL aggregates to have a median size of at least 200 nm.

According to another aspect of the present disclosure the cholesterol lowering medication is selected from the group consisting of a healthy Nordic diet, a low sucrose diet, a PCSK9 inhibitor, a HMG CoA reductase inhibitor, a selective cholesterol absorption inhibitor, a bile-acid binding resin, and combinations thereof.

The present disclosure describes also a method comprising: providing LDL particles from a human blood plasma sample of a human subject that has been taking a HMG CoA reductase inhibitor, a selective cholesterol absorption inhibitor, or a bile-acid binding resin; mixing the LDL particles with sphingomyelinase enzyme in a solution at acidic pH; detecting formation of LDL aggregates in said solution; measuring the size of the detected LDL aggregates; and if the LDL aggregates have a median size of at least 500 nm, continue administering to the human subject a therapeutically effective amount of the HMG CoA reductase inhibitor, selective cholesterol absorption inhibitor, or bile-acid binding resin; and if the LDL aggregates have a median size of below 500 nm, discontinue administration to the human subject a therapeutically effective amount of the HMG CoA reductase inhibitor, selective cholesterol absorption inhibitor, or bile-acid binding resin and administer a medication selected from the group consisting of a healthy (Nordic) diet, a low sucrose diet, and a PCSK9 inhibitor, or continue administering to the human subject a therapeutically effective amount of the cholesterol lowering medication in combination with a medication selected from the group consisting of a healthy (Nordic) diet, a low sucrose diet, and a PCSK9 inhibitor.

Example 1. Measurement of the Susceptibility of LDL to Aggregate Ex Vivo

Figure 4A:
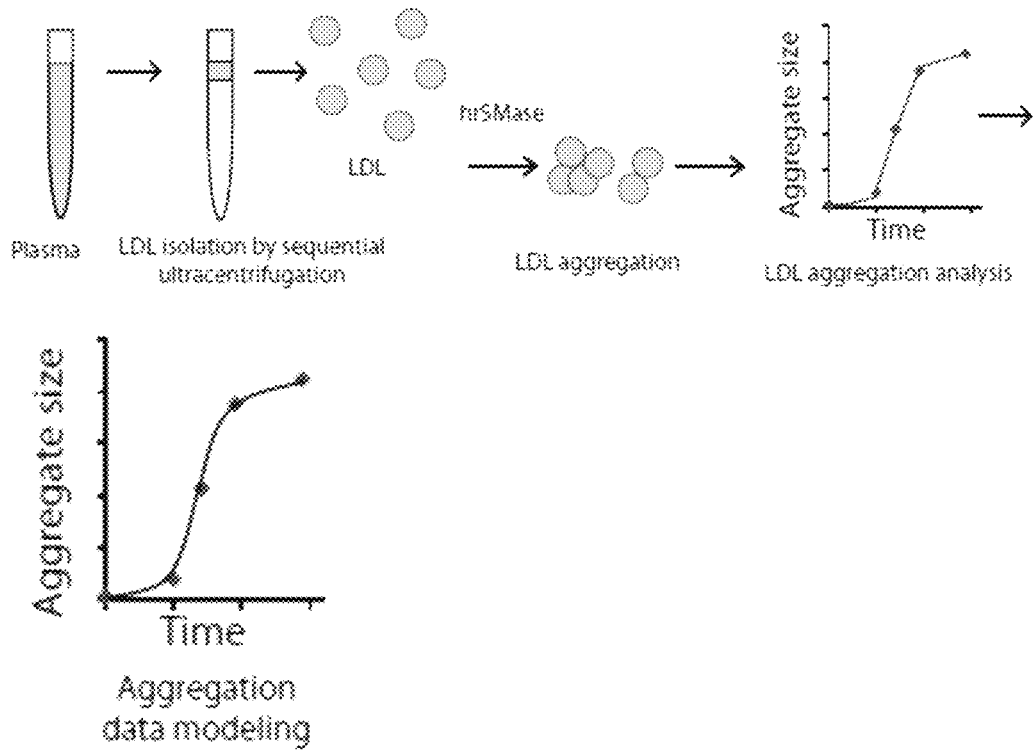
FIG. 4A. Measurement of the susceptibility of LDL derived from healthy human subjects and from patients with coronary artery disease (CAD) to aggregate ex vivo. LDL was isolated from blood plasma by ultracentrifugation and aggregation was induced by incubation with hrSMase at pH 5.5. The size of LDL particles was measured before hrSMase treatment (time=0 h), and formation of LDL aggregates was followed in real time by measuring their sizes with DLS.
Figure 4B:
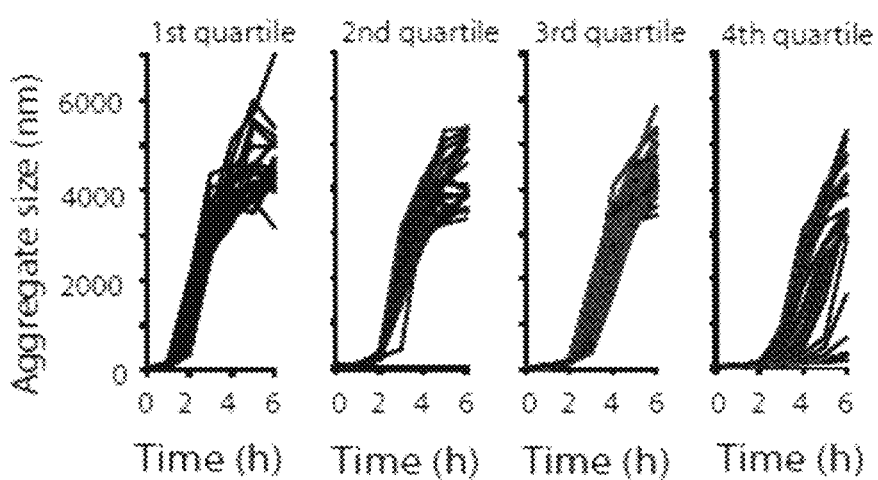
FIG. 4B. Measurement of the susceptibility of LDL derived from healthy human subjects and from patients with CAD to aggregate ex vivo. LDL particles were isolated from 100 plasma samples collected from the Finnish Health 2000 Health Examination Survey and the aggregation susceptibility of the particles was analysed. Based on LDL aggregate size at 2 h, the particles were divided into quartiles.
Figure 4C:
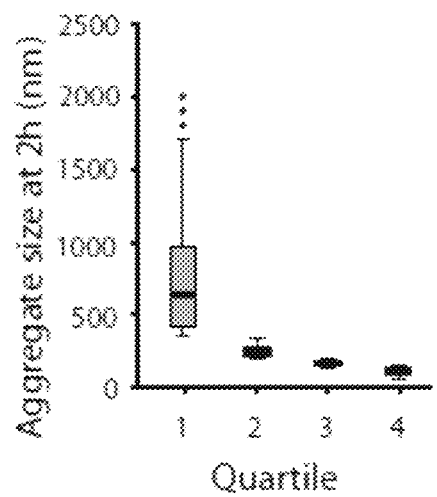
FIG. 4C. Measurement of the susceptibility of LDL derived from healthy human subjects and from patients with CAD to aggregate ex vivo. Size distributions of LDL aggregates are presented at the 2-h time point. The box encompasses the middle 50% of the measured values; the horizontal line within each box shows the median of the measured values; each whisker encompasses the most extreme data point that is still no further from the margins of the box than 1.5 times the interquartile range. Statistical differences between the groups were determined using Kruskal-Wallis test followed by Dunn's test. P<0.001 by Kruskal-Wallis test; * P<0.05, *** P<0.001 by Dunn's test.
Figure 5A:
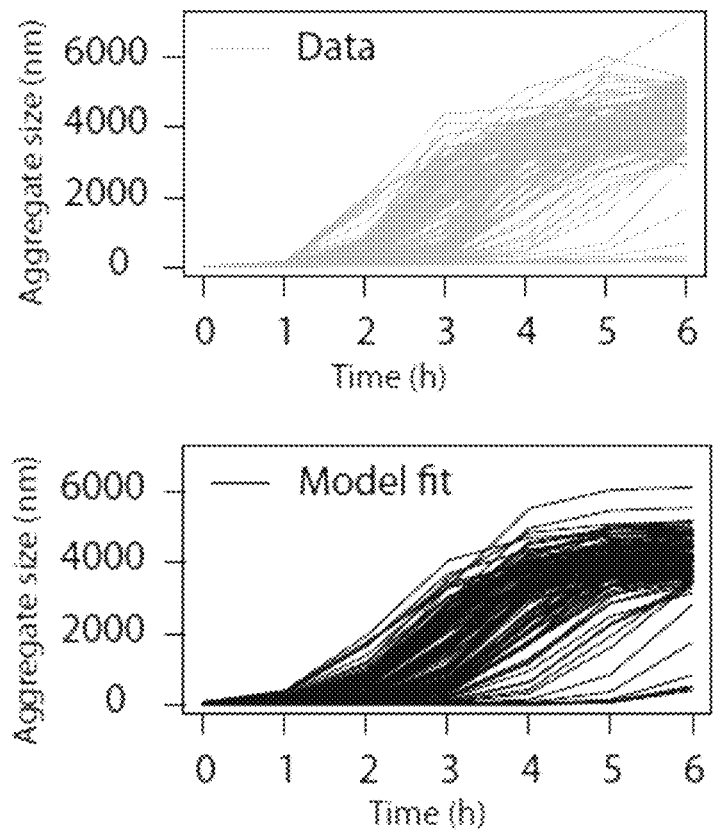
FIG. 5A. Analysis of inter-individual variability in LDL aggregation. LDL aggregation data (upper panel) and the corresponding logistic mixed-effects models (lower panel) in the Health 2000 dataset (n=100).
Figure 5B:
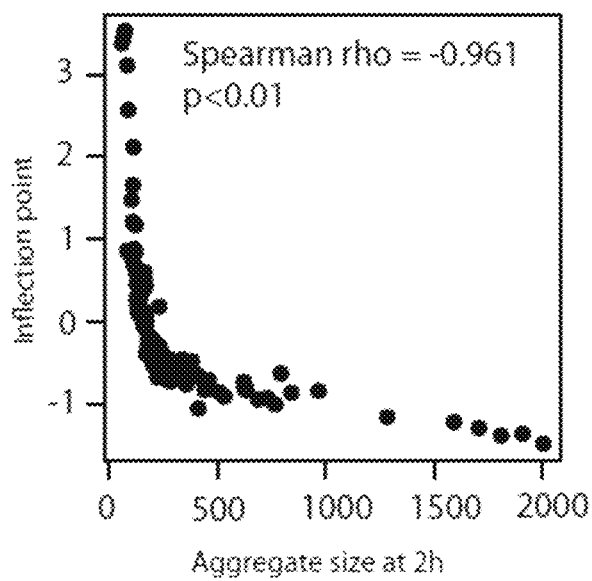
FIG. 5B. Analysis of inter-individual variability in LDL aggregation. Correlation of the point of inflection (vertical axis) and the 2 h-aggregate size (horizontal axis) in the Health 2000 dataset.

A novel, reproducible method to quantify donor-to-donor variation in the susceptibility of LDL particles to aggregate was generated. The method is based on analysis of aggregation kinetics of LDL isolated from plasma by ultracentrifugation. LDL aggregation is induced by hrSMase and the growth of the aggregates is measured by dynamic light scattering (DLS) (FIG. 4a). Other agents to modify LDL ex vivo produced far smaller aggregates with negligible discrimination between individuals (FIGS. 1a-e).

hrSMase-based assay was used to screen LDL aggregation susceptibility in samples derived from the Finnish Health 2000 Health Examination Survey, which comprised largely healthy individuals (n=100, Table 1, FIG. 4b). A population-based generalized mixed-effect model was estimated, from which the inter-individual variation in aggregation susceptibility of LDL was calculated (FIG. 5a). These data revealed that inflection point in the aggregate size vs. incubation time curves readily distinguished the aggregation susceptibility of the different LDL samples. Further, it was found that LDL aggregate size at 2-h time point correlated tightly and significantly with the inflection point (FIG. 5b, rho=−0.961, $p<0.001$). Importantly, the extent of aggregation at 2 h clearly identified subjects having extremely aggregation-prone LDL particles (FIG. 4c, Quartile 1).

TABLE 1

Clinical characteristics of Health 2000 Health Examination survey participants assessed in this study.

| Characteristics | HEALTH 2000 |
|---|---|
| Number of subjects[1] | 100 |
| Gender (male) [1] | 50 (50%) |
| Age (years) [2] | 40 (33-48) |
| Current smoker[1] | 15 (15%) |
| Blood pressure: syst/diast (mm Hg) [2] | 121/78 (110-132/68-85) |

TABLE 1-continued

Clinical characteristics of Health 2000 Health Examination survey participants assessed in this study.

| Characteristics | HEALTH 2000 |
|---|---|
| BMI (kg/m$^2$) [2] | 24.2 (22.5-28.1) |
| Glucose (mmol/L) [2] | 5.2 (5.0-5.5) |
| Diabetes[1] | 1 (1%) |
| Statin (n = 91) [1] | 4 (4%) |
| Total cholesterol (mmol/L) [2] | 5.5 (4.8-6.5) |
| LDL-C (mmol/L) [2] | 3.1 (2.6-4.0) |
| HDL-C (mmol/L) [2] | 1.3 (1.1-1.6) |
| TG (mmol/L) [2] | 1.3 (0.9-1.9) |
| C-reactive protein (mg/L) [2] | 0.6 (0.2-1.8) |

[1]Number of cases (%)
[2]Median (range)

Example 2. The Susceptibility of LDL to Aggregate Predicts Future Cardiovascular Deaths Next the aggregation susceptibility of LDL isolated from plasma samples derived from patients with clinically diagnosed CAD was measured. The samples were from a nested case-control study (13), which had been designed using samples from the Finnish Corogene study (14). The nested case-control study included all patients who had experienced coronary death within an average follow-up of 2.5 years. Control patients were selected from the group who had no cardiovascular events during the follow-up period and they were pairwise matched based on conventional CAD risk factors, statin use, and coronary stenosis index (Table 2). The plasma samples selected for this study (n=48) were from non-diabetic males, all of whom had ≥50% coronary stenosis.

TABLE 2

Baseline characteristics of Corogene study patients assessed in this study.

| Characteristics | CAD Death | Stable CAD |
|---|---|---|
| Number of patients | 24 | 24 |
| Gender (male) [1] | 24 (100%) | 24 (100%) |
| Age (years) [2] | 66 (60-73) | 66 (60-73) |
| Current smoker[1] | 8 (33%) | 8 (33%) |
| Hypertension[1] | 18 (75%) | 13 (54%) |
| BMI (kg/m$^2$) [2] | 26.1 (25.1-29.8) | 25.6 (24.8-27.4) |
| Diabetes[1] | 0 (0%) | 0 (0%) |
| Statin[1] | 13 (54%) | 13 (54%) |
| Coronary Stenosis Index[2] | 14 (3-28) | 15 (2-42) |
| Total cholesterol (mmol/L) [2] | 3.5 (2.9-4.1) | 3.8 (3.1-4.4) |
| LDL-C (mmol/L) [2] | 2.1 (1.6-2.5) | 2.1 (1.6-2.7) |
| HDL-C (mmol/L) [2] | 0.8 (0.7-1.0) | 0.9 (0.9-1.1) |
| TG (mmol/L) [2] | 2.5 (2.1-2.8) | 2.9 (1.9-3.7) |
| C-reactive protein (mg/L) [2] | 4.5 (2.3-12) | 0.8 (0.7-2.0) |

[1]Number of cases (%)
[2]Median (range)

Figure 4D:
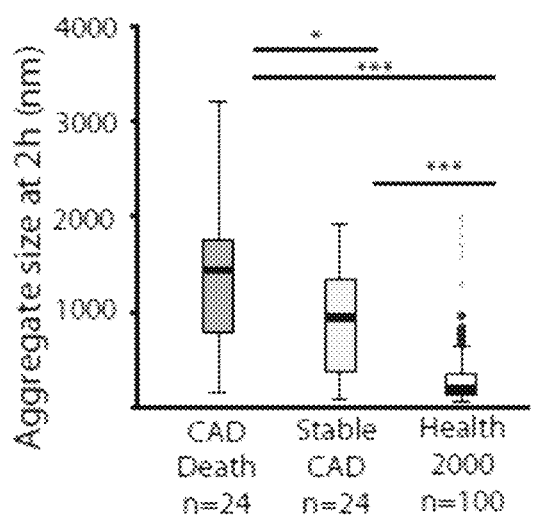
FIG. 4D. Measurement of the susceptibility of LDL derived from healthy human subjects and from patients with CAD to aggregate ex vivo. Patients (n=48) from the Corogene study, having >50% coronary artery stenosis were divided into two groups: 1) CAD Death group, in which patients died of a coronary event during an average 2.5-year follow-up period, and 2) Stable CAD group, in which the patients did not have cardiovascular events during the follow-up period. The patients were matched for the conventional cardiovascular risk factors. LDL was isolated and LDL aggregation was induced by treatment with hrSMase. The box plot diagram shows the distribution of aggregate sizes after incubation for 2 h in the two groups from Corogene study and in 100 subjects from the Health 2000 study (all quartiles from panel c combined). Statistical differences between the groups were determined using Kruskal-Wallis test followed by Dunn's test. P<0.001 by Kruskal-Wallis test; * P<0.05, *** P<0.001 by Dunn's test.

Large inter-individual differences in the aggregation susceptibility of the isolated LDL particles was again observed. Importantly, in the CAD Death group, LDL particles aggregated significantly faster than in the Stable CAD group, the median sizes of the aggregates after incubation for 2 h being 1500 nm (range 150-3200 nm) and 940 nm (range 90-1990 nm), respectively (FIG. 4d). Moreover, the 2 h aggregate sizes of LDL samples in both CAD groups were significantly higher than in the 100 LDL samples obtained from the Health 2000 study (median 200 nm; range 60-2000 nm) (FIG. 4d). LDL aggregation at 2 h was not associated with the initial sizes of LDL particles, nor with plasma concentrations of LDL-C, apoB-100, C-reactive protein (hsCRP), or lipoprotein (a), nor with statin use, age, or smoking, but showed a negative correlation with plasma triglyceride levels (FIG. 6 and Table 3).

TABLE 3

Clinical characteristics of SYSDIET-study participants assessed in this study.

| Characteristics | Control Diet | | Healthy Nordic diet | |
|---|---|---|---|---|
| Number of subjects[1] | 24 | | 33 | |
| Male/female[1] | 8/16 (33%/66%) | | 13/20 (39%/61%) | |
| Age (years) [2] | 57 (50-61) | | 54 (45-59) | |
| Current smoker[1] | 0 (0%) | | 0 (0%) | |
| Diabetes[1] | 0 (0%) | | 0 (0%) | |
| Study weeks | 0 | 18/24 | 0 | 18/24 |
| Blood pressure: syst/diast (mm Hg) [2] | 130/86 (124-143/74-93) | 128/84 (121-136/78-92) | 133/88 (124-138/81-95) | 129/86 (123-140/78-91) |
| BMI (kg/m$^2$) [2] | 31.6 (29.6-34.0) | 32.0 (30.5-34.5) | 29.7 (28.5- 33.1) | 29.8 (28.1-33.6) |
| Glucose (mmol/L) [2] | 5.6 (5.4-6.2) | 5.6 (5.3-6.1) | 5.9 (5.4-6.2) | 5.6 (5.3-6.1) |
| Statin[1] | 7 (29%) | 7 (29%) | 7 (21%) | 7 (21%) |
| Total cholesterol (mmol/L)[2] | 5.4 (4.7-6.3) | 5.5 (4.6-6.0) | 5.2 (4.9-6.1) | 5.1 (4.6-5.8) |
| LDL-C (mmol/L) [2] | 3.4 (3.0-4.1) | 3.7 (2.5-4.0) | 3.2 (2.6-4.1) | 3.0 (2.5-3.6) |
| HDL-C (mmol/L) [2] | 1.2 (1.1-1.5) | 1.3 (1.1-1.7) | 1.5 (1.2-1.7) | 1.6 (1.3-1.8) |
| TG (mmol/L) [2] | 1.2 (1.0-1.9) | 1.4 (0.9-1.8) | 1.4 (0.8-1.9) | 1.3 (1-1.7) |
| C-reactive protein (mg/L) [2] | 1.7 (0.9-4.2) | 1.8 (1.2-2.7) | 1.5 (0.8-2.8) | 1.6 (0.8-4.1) |

[1]Number of cases (%)
[2]Median (range)

Figure 7A:
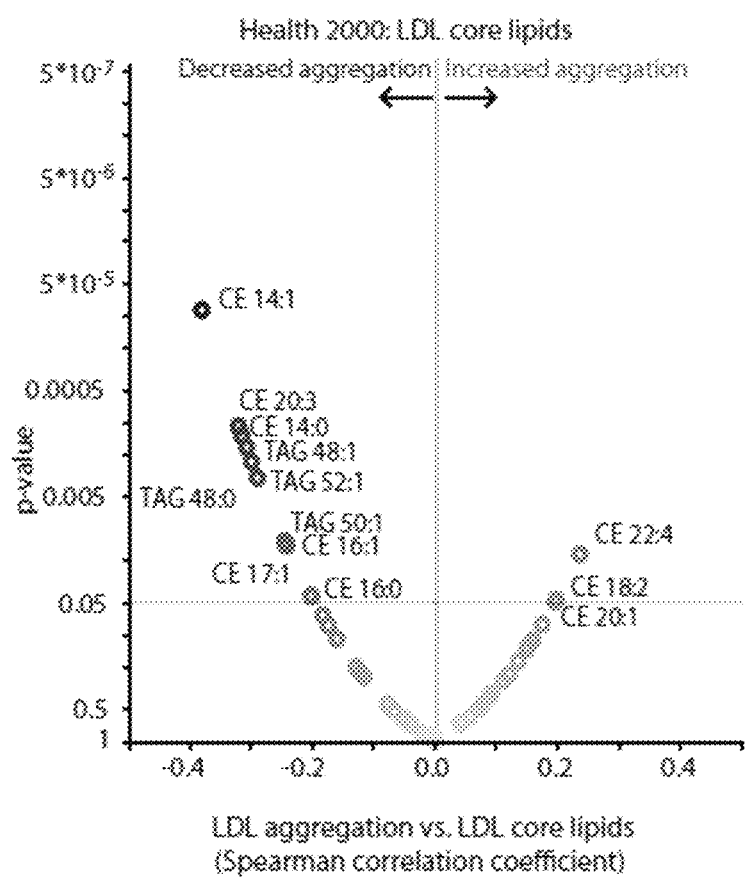
FIG. 7A. The susceptibility of LDL to aggregate strongly correlates with the core lipid composition of the particles. Volcano plots showing Spearman correlation coefficients of LDL aggregate size at 2 h vs. LDL core lipids in Health 2000 samples. Circles to the right of the value 0 indicate positive correlations, and circles to the left of the value 0 indicate negative correlations. The identities of only those lipids with significance correlation values (p<0.05) are indicated. CE=cholesteryl ester, TAG=triacylglycerol.
Figure 7B:
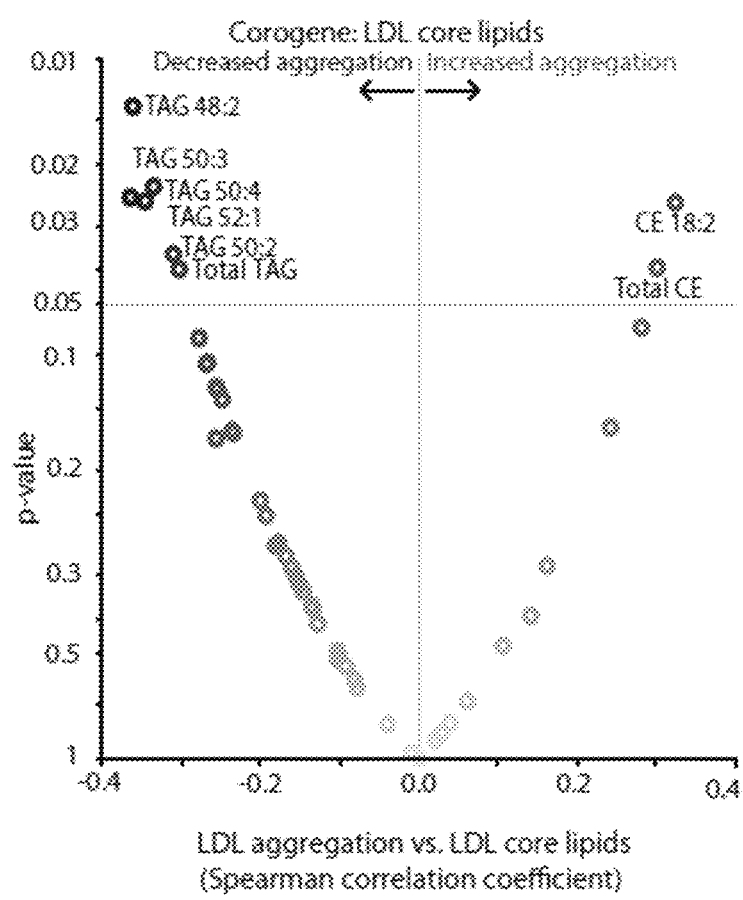
FIG. 7B. The susceptibility of LDL to aggregate strongly correlates with the core lipid composition of the particles. Volcano plots showing Spearman correlation coefficients of LDL aggregate size at 2 h vs. LDL core lipids in Corogene samples. Circles to the right of the value 0 indicate positive correlations, and circles to the left of the value 0 indicate negative correlations. The identities of only those lipids with significance correlation values (p<0.05) are indicated. CE=cholesteryl ester, TAG=triacylglycerol.

Example 3. The Susceptibility of LDL Particles to Aggregate Strongly Associates with the Particle Lipid Composition The surface monolayer of LDL particles comprises phospholipids, unesterified cholesterol (UC), ceramides (Cer), and the major structural apolipoprotein, apoB-100 (FIG. 3a). Phosphatidylcholines (PC) are the major phospholipid class, followed by sphingomyelins (SM), and lysophosphatidylcholines (LPC). The surface also contains small amounts of other classes of phospholipids and ceramides. The particle core contains mainly cholesteryl esters (CE) and triacylglycerols (TAG). The composition of the isolated LDL particles from both studies described above was determined by quantitative mass spectrometry-based lipidomics. Volcano plots show the significant ($p<0.05$) correlations between LDL aggregation and the molar percentages of specific lipids of the LDL surface (FIG. 3b,c) and core (FIG. 7a,b). Several sphingolipids (SMs and various forms of Cer) correlated positively and various phosphatidylcholine (PC) species negatively with LDL aggregation in both cohorts. Regarding the core lipids of LDL, the degree of LDL aggregation correlated negatively particularly with several 48-52 carbon TAGs in both cohorts (FIG. 7a, b).

Example 4. Direct Enrichment LDL with Different Phospholipids Changes Aggregation Susceptibility of LDL and Conformation of apoB-100

Figure 8A:
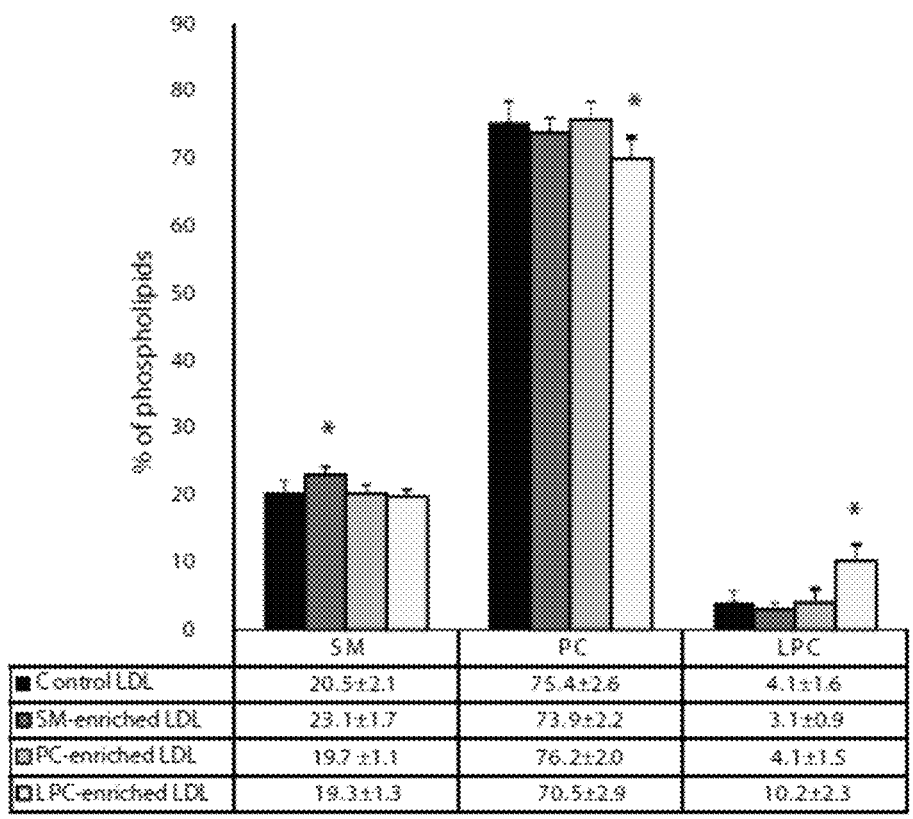
FIG. 8A. Direct enrichment of isolated LDL ex vivo with different phospholipids changes aggregation susceptibility and apoB-100 conformation at baseline and after incubation with hrSMase. The amounts of SM, PC, and LPC in LDL before and after treatment with SM-, PC-, and LPC-vesicles was determined by mass spectrometry. n=4, t-test was used to compare the groups.
Figure 8B:
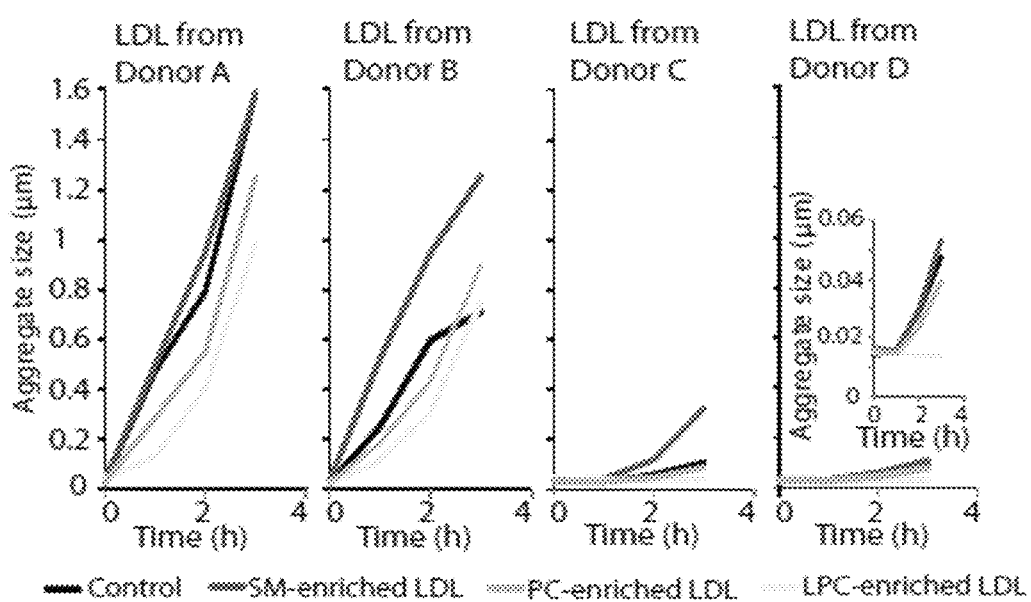
FIG. 8B. LDL particles from four healthy volunteer blood donors were treated with no vesicles (Control) or with SM-, PC- or LPC-vesicles after which the LDL particles were re-isolated. Control LDL and the SM-, PC- and LPC-enriched LDL particles were treated with hrSMase and particle aggregation was determined by DLS.
Figure 8C:
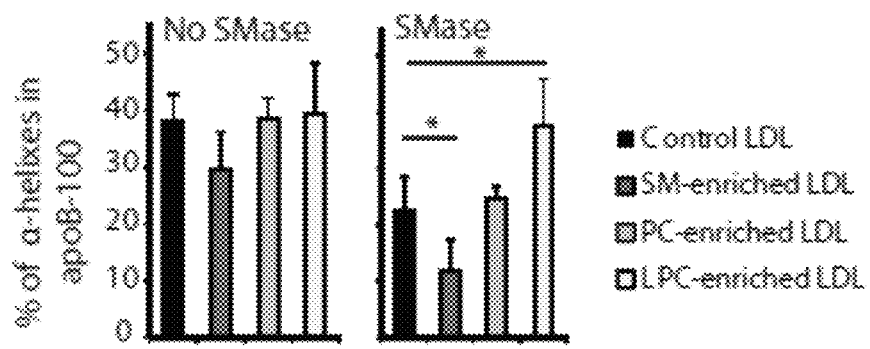
FIG. 8C. The average±SEM amount of α-helix in control LDL and in SM-, PC- and LPC-enriched LDL before and after SMase-treatment was determined by circular dichroism (n=6, except for LPC-enriched n=4), t-test was used to compare groups. * indicates p-value <0.05.
Figure 8D:
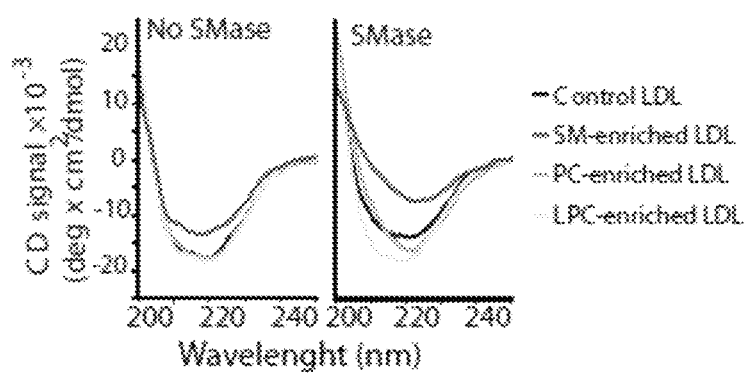
FIG. 8D. Representative CD spectra of the LDL samples described in FIG. 8C.
Figure 8E:
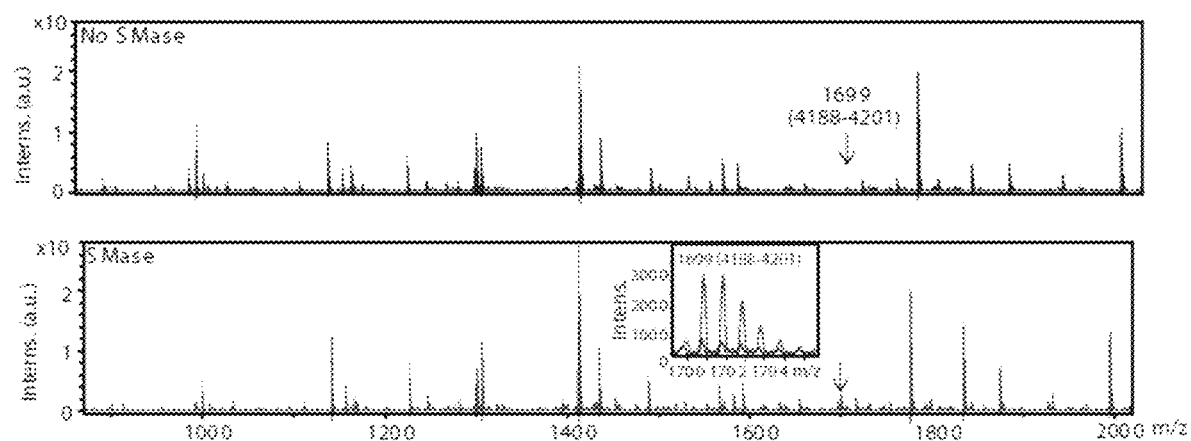
FIG. 8E. Native (upper panel) and SMase-treated (below panel) LDL was trypsinized shortly and the peptides released from the particles were identified with mass spectrometry. Typical spectra of the particles are shown from three independent experiments. The inset shows enlargement of an area, where a peptide was identified in only SMase-treated particles. The released peptide was identified as HLIDSLIDFLNFPR (residues 4188-4201 of apoB-100). * indicates p-value <0.05.

The inventors next enriched LDL isolated from four healthy volunteers with SM 18:1/16:0, PC 16:0/18:1, or LPC 16:0 to determine the effect of these lipids on LDL aggregation. Changes in the relative proportions of phospholipids in these lipid-enriched LDL particles were small (FIG. 8a) and the final compositions were well within ranges observed in LDL. Although the aggregability of control LDL from the four donors varied considerably (FIG. 8b, black lines), in each case the LDL preparations enriched with SM became more susceptible to aggregate during incubation with hrSMase, while LDL preparations enriched with PC or LPC became less susceptible. It was also found that enrichment of LDL with SM enhanced SMase-induced conformational changes in apoB-100 (FIGS. 8c, d).

Example 5. In Human Subjects, Decrease in LDL-SM by Diet or PCSK9 Inhibitor Decreases LDL Aggregation Susceptibility To determine if a change in LDL lipid composition changes the aggregation susceptibility of LDL, samples from two different interventions: 1) SYSDIET, a dietary intervention, in which healthy volunteers with features of the metabolic syndrome were randomly assigned to either a Healthy Nordic diet (n=33) or to a Control diet (n=24) for 18 or 24 weeks, and 2) EQUATOR, a randomized placebo-controlled phase II trial of a fully human monoclonal antibody RG7652 that inhibits the function of proprotein convertase subtilisin/kexin type 9 (PCSK9, n=25) or placebo (n=15) before and 29 days after the treatment/placebo were analysed.

Figure 9A:
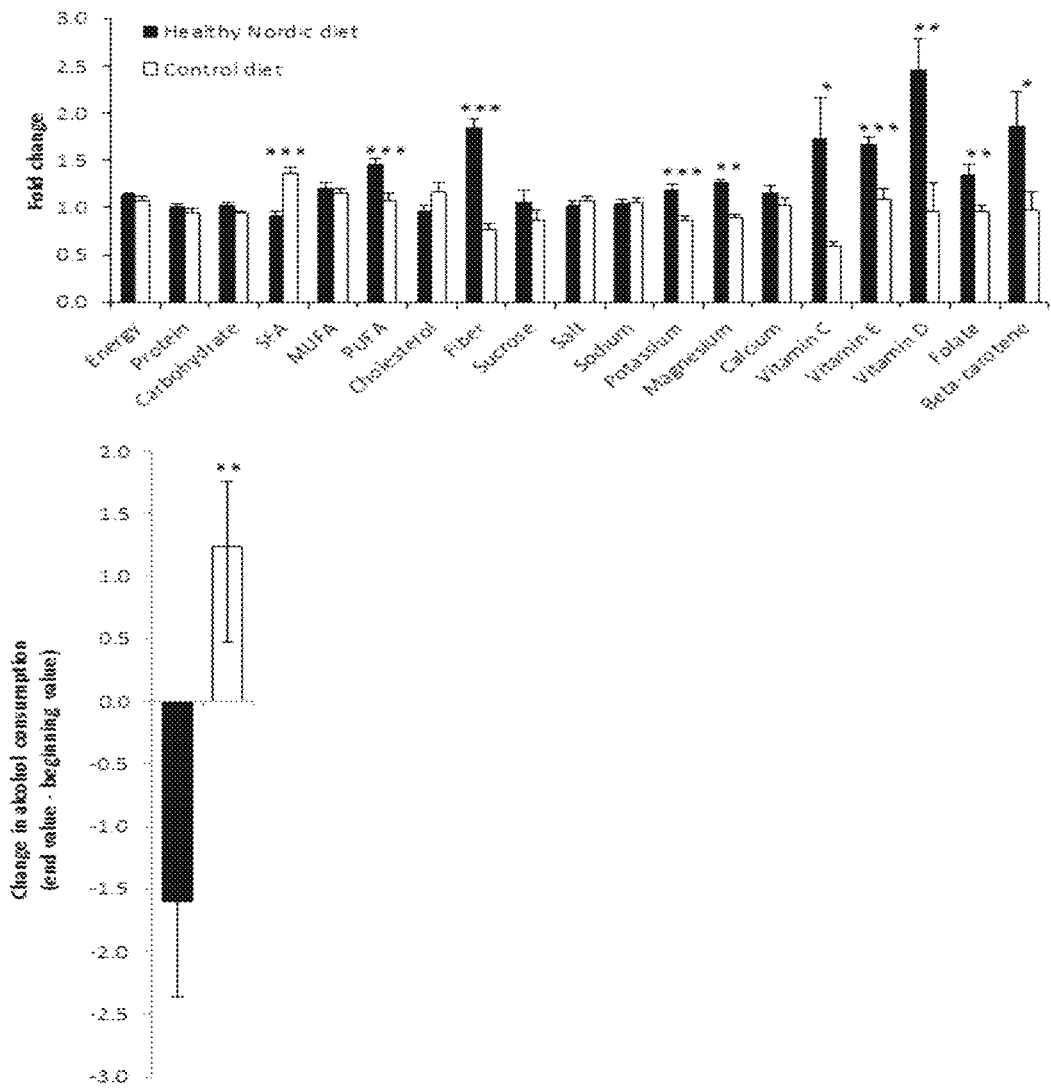
FIG. 9A. Changes in the reported consumption of different micro- and macronutrients and their correlation with LDL composition and aggregation in SYSDIET-study. Changes in intake of the various micro- and macronutrients were calculated by dividing the 18- or 24-week value by the corresponding 0-week value (upper panel), except for alcohol consumption, which was calculated by subtraction, because some study subjects consumed no alcohol (below panel). The columns show averages±SEMs. Healthy Nordic diet, n=33, Control diet, n=24. * P<0.05,  P<0.01, * P<0.001 by Student's t-test. The p-values were corrected for false discovery rate using Benjamini-Hochberg method.
Figure 9B:
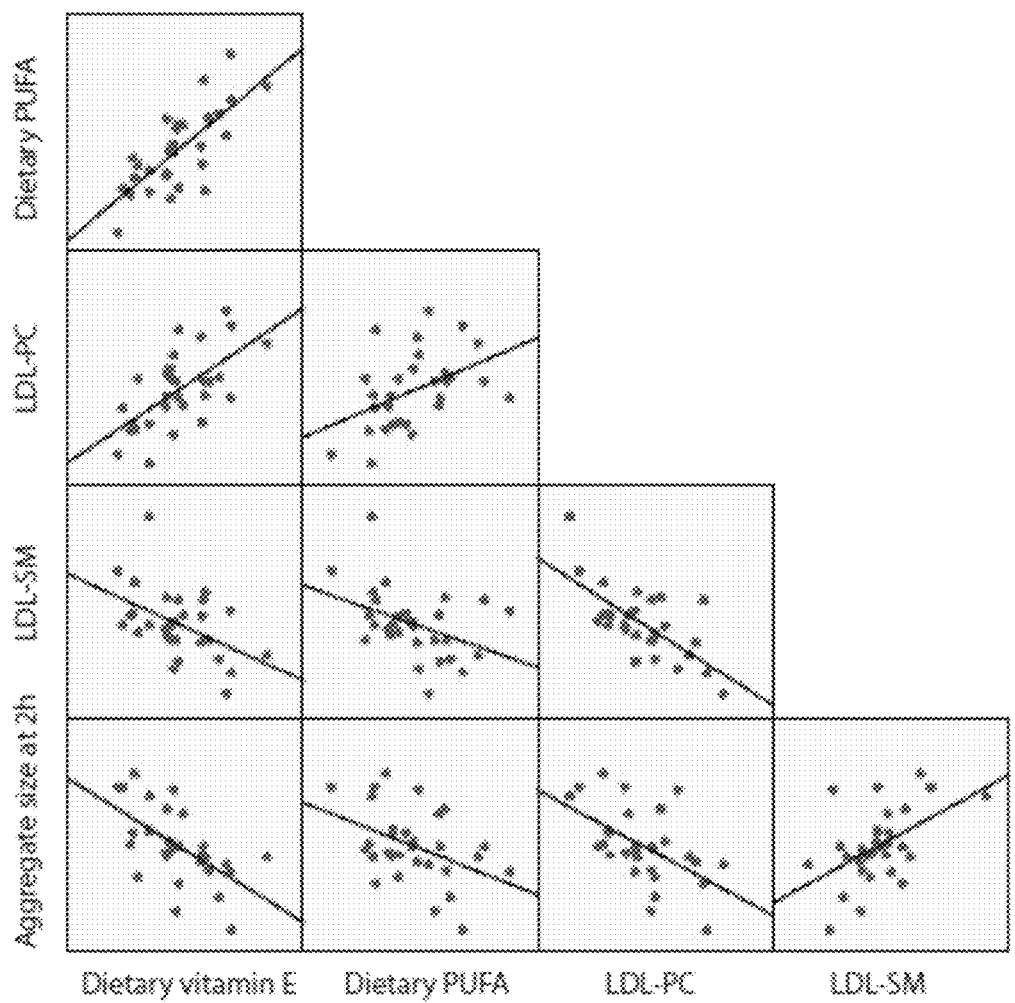
FIG. 9B. Changes in the reported consumption of different micro- and macronutrients and their correlation with LDL composition and aggregation in SYSDIET-study. Association of changes in dietary vitamin E and dietary PUFA with LDL-PC and LDL-SM, as well as with LDL aggregation.
Figure 10A:
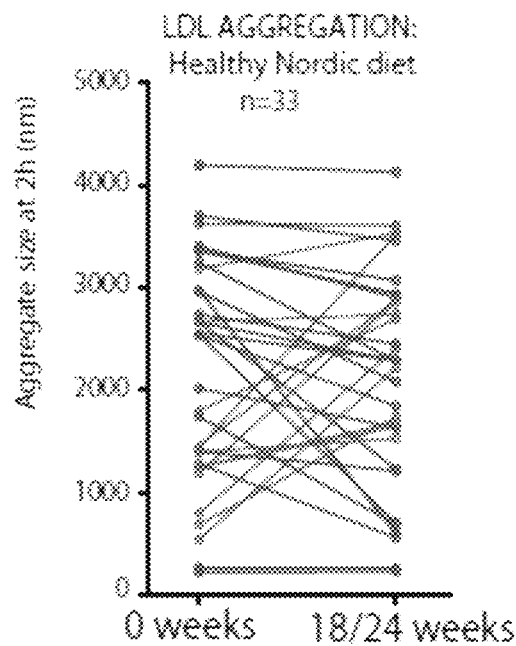
FIG. 10A. Dietary intervention (SYSDIET-study) and proprotein convertase subtilisin/kexin type 9 (PCSK9) inhibition (EQUATOR study) in human subjects improves the lipid composition of LDL and renders LDL less susceptible to aggregation. Plasma samples were obtained from 33 participants on an isocaloric healthy Nordic diet and from 24 participants on a control diet participating in the SYSDIET-study. In addition, plasma samples were obtained from 25 patients receiving a monoclonal antibody (RG7652) inhibiting the function of PCSK9, and from 15 patients receiving placebo. LDL was isolated, and aggregation analysed from samples before and after the diet/treatment period. LDL aggregate sizes at the 2-h time point are shown in the diet group before and after the diet period. Each line represents one subject, and downward lines show decreases and upward lines increases in aggregate size.
Figure 10B:
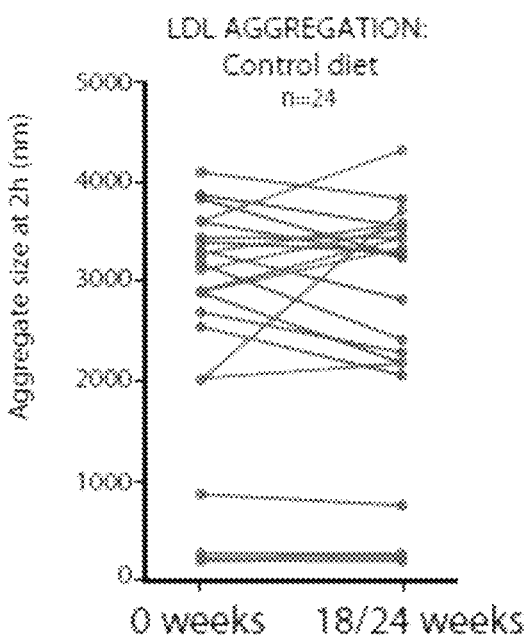
FIG. 10B. The same study set as in FIG. 10A, but LDL aggregate sizes at the 2-h time point are shown in the control group before and after the diet period. Each line represents one subject, and downward lines show decreases and upward lines increases in aggregate size.
Figure 10C:
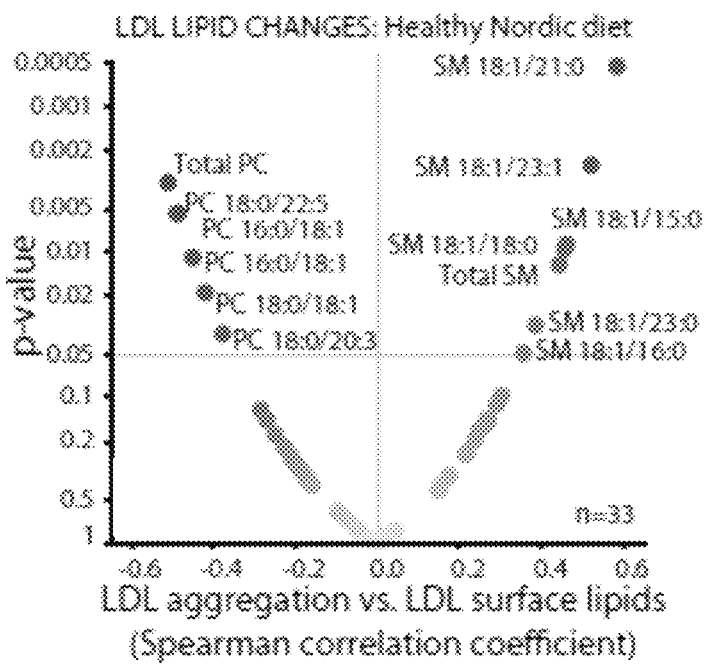
FIG. 10C. A volcano plot showing the Spearman correlation coefficients of LDL aggregate size at 2 h vs. LDL surface lipids in the SYSDIET study. PC=phosphatidylcholine, PE=phosphatidylethanolamine, SM=sphingomyelin.
Figure 10D:
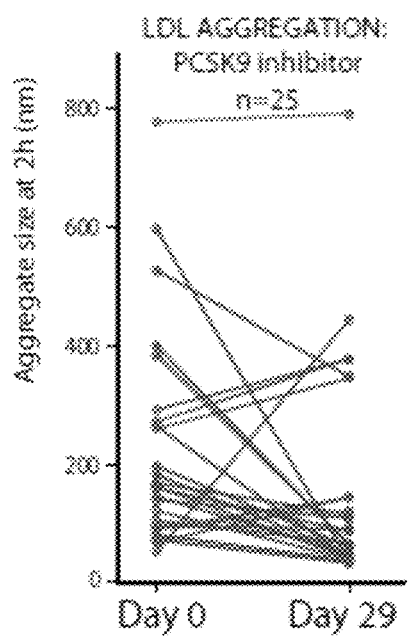
FIG. 10D. The same study set as in FIGS. 10A and B, but now LDL aggregate sizes at the 2-h time point are shown in the PSCK9 inhibitor group before and after the treatment period. Each line represents one subject.
Figure 10E:
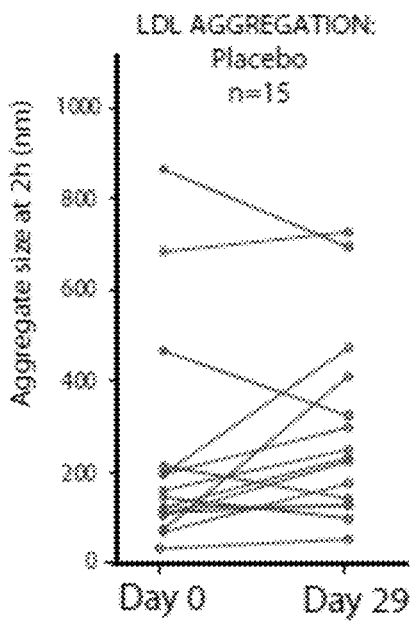
FIG. 10E. The same study set as in FIGS. 10A and B, but now LDL aggregate sizes at the 2-h time point are shown in the placebo group before and after the treatment period. Each line represents one subject.
Figure 10F:
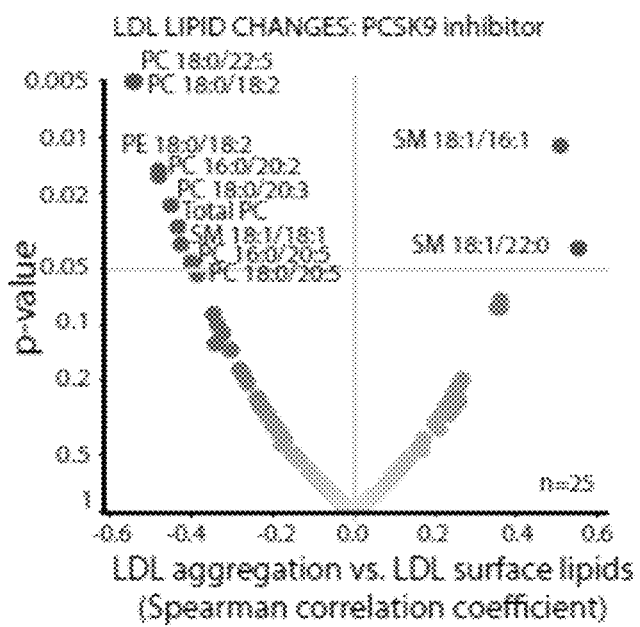
FIG. 10F. A volcano plot showing the Spearman correlation coefficients of LDL aggregate size at 2 h vs. LDL surface lipids in the EQUATOR study. PC=phosphatidylcholine, PE=phosphatidylethanolamine, SM=sphingomyelin.
Figure 11A:
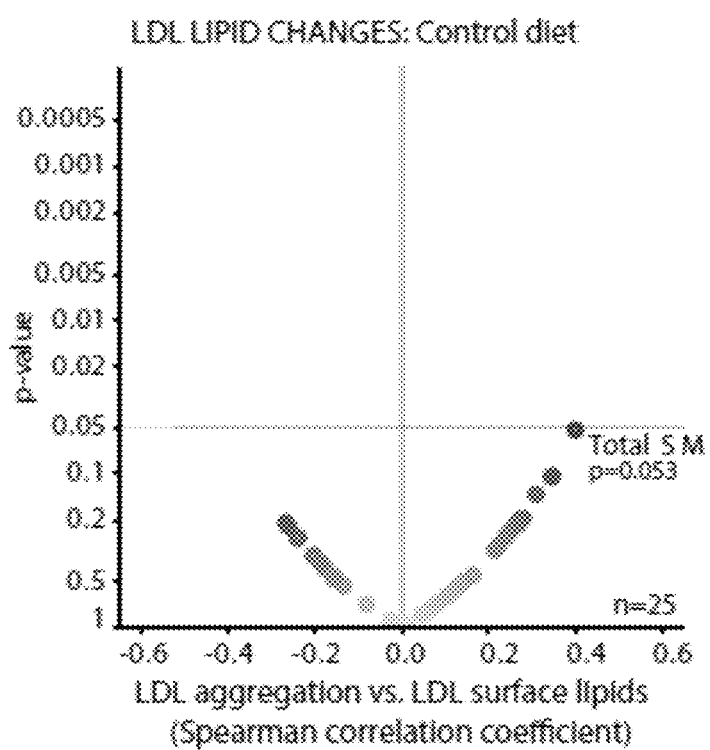
FIG. 11A. Correlation between the changes in the susceptibility of LDL to aggregate and changes in LDL surface lipid composition. Volcano plots showing Spearman correlation coefficients of changes in LDL aggregate size at 2 h vs. changes in LDL surface lipids in the control samples derived from the participants of the SYSDIET study. The identities of only those lipids with significance correlation values (p<0.05) are indicated.

First, the aggregation of LDL from plasma samples that had been collected from the Finnish participants in the SYSDIET study was analysed. Table 4 shows the clinical characteristics of these subjects at baseline and at the end of the study and FIG. 9a shows the changes in the macro- and micro-nutrient compositions of what each subject consumed based on food diaries at the beginning and at the end of the study. In the Healthy Nordic diet group, LDL aggregation decreased in two thirds of the participants, whereas in the control group, only small changes in LDL aggregation were observed (FIG. 10a,b). To estimate how much of the changes in LDL aggregation can be attributed to the dietary changes, a multivariate model was constructed using data from the subjects in the Healthy Nordic diet group. The best model included just two components from the food diaries: changes in dietary vitamin E and changes in dietary sucrose (Table 5), where decreased aggregation susceptibility was associated with increased dietary vitamin E and decreased dietary sucrose consumption. An increase in dietary vitamin E is considered a good marker of increased consumption of vegetable oils rich in polyunsaturated fatty acids, and both were significantly associated with increased proportion of PCs and decreased proportion of SMs in plasma LDL particles (FIG. 9b). These lipidomics changes were also associated with decreased LDL aggregation susceptibility in the Healthy Nordic diet group (FIG. 9c and FIG. 10), but no significant associations were observed in the control group (FIG. 11a).

Figure 11B:
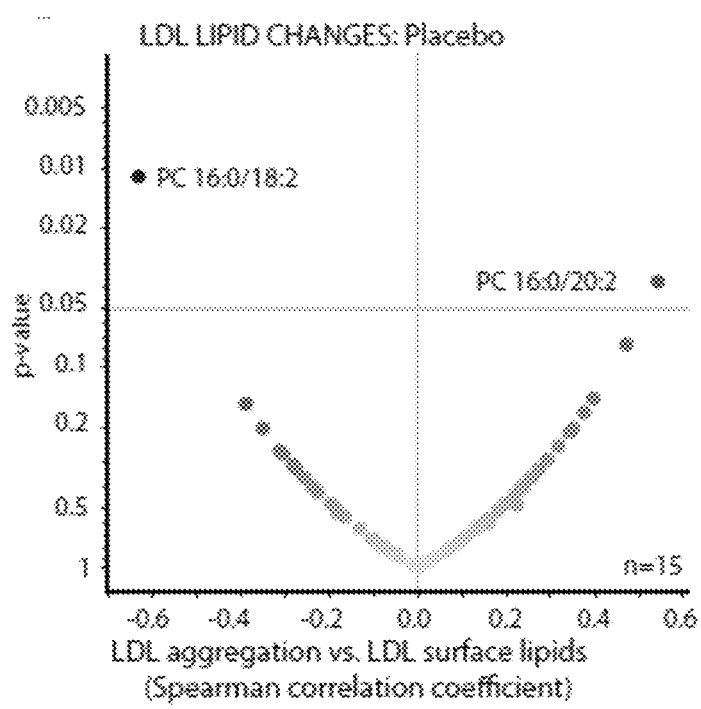
FIG. 11B. Correlation between the changes in the susceptibility of LDL to aggregate and changes in LDL surface lipid composition. Volcano plots showing Spearman correlation coefficients of changes in LDL aggregate size at 2 h vs. changes in LDL surface lipids in placebo samples derived from the participants of the EQUATOR study. The identities of only those lipids with significance correlation values (p<0.05) are indicated.

Inhibition of PCSK9 is known to strikingly lower LDL-C, and recently the present inventors found that the inhibition also influences plasma and lipoprotein phospholipid composition. In the treatment group, but not in the placebo group, a significant decrease in LDL aggregation susceptibility was observed in most subjects (FIG. 9d, e), the change in aggregation susceptibility between the groups being statistically significant (p=0.035). The decrease in LDL aggregation in the treatment group correlated with an increase in several PC species and a decrease in several SM species (FIG. 9f). In the control group, only PC 16:0/18:2 correlated significantly with decreased LDL aggregation susceptibility (FIG. 11b).

TABLE 4

Clinical characteristics of the SYSDIET-study participants assessed in this study.

| Characteristics | Control Diet | | Healthy Nordic diet | |
| --- | --- | --- | --- | --- |
| Number of subjects[1] | 24 | | 33 | |
| Male/female[1] | 8/16 (33%/66%) | | 13/20 (39%/61%) | |
| Age (years) [2] | 57 (50-61) | | 54 (45-59) | |
| Current smoker[1] | 0 (0%) | | 0 (0%) | |
| Diabetes[1] | 0 (0%) | | 0 (0%) | |
| Study weeks | 0 | 18/24 | 0 | 18/24 |
| Blood pressure: syst/diast (mm Hg) [2] | 130/86 (124-143/74-93) | 128/84 (121-136/78-92) | 133/88 (124-138/81-95) | 129/86 (123-140/78-91) |
| BMI (kg/m$^2$) [2] | 31.6 (29.6-34.0) | 32.0 (30.5-34.5) | 29.7 (28.5-33.1) | 29.8 (28.1-33.6) |

TABLE 4-continued

Clinical characteristics of the SYSDIET-study participants assessed in this study.

| | | | | |
|---|---|---|---|---|
| Glucose (mmol/L) [2] | 5.6 (5.4-6.2) | 5.6 (5.3-6.1) | 5.9 (5.4-6.2) | 5.6 (5.3-6.1) |
| Statin1 | 7 (29%) | 7 (29%) | 7 (21%) | 7 (21%) |
| Total cholesterol (mmol/L)[2] | 5.4 (4.7-6.3) | 5.5 (4.6-6.0) | 5.2 (4.9-6.1) | 5.1 (4.6-5.8) |
| LDL-C (mmol/L)[2] | 3.4 (3.0-4.1) | 3.7 (2.5-4.0) | 3.2 (2.6-4.1) | 3.0 (2.5-3.6) |
| HDL-C (mmol/L)[2] | 1.2 (1.1-1.5) | 1.3 (1.1-1.7) | 1.5 (1.2-1.7) | 1.6 (1.3-1.8) |
| TG (mmol/L) [2] | 1.2 (1.0-1.9) | 1.4 (0.9-1.8) | 1.4 (0.8-1.9) | 1.3 (1-1.7) |
| C-reactive protein (mg/L) [2] | 1.7 (0.9-4.2) | 1.8 (1.2-2.7) | 1.5 (0.8-2.8) | 1.6 (0.8-4.1) |

[1]Number of cases (%)
[2]Median (interquartile range)

TABLE 5

Multiple regression explaining the effect of dietary changes on changes in the 2 h-aggregate size in the Sysdiet group.

| | |
|---|---|
| Multiple R | .703 |
| Multiple $R^2$ | .494 |
| Adjusted $R^2$ | .456 |
| Standard error of estimate | 773.289 |

Analysis of Variance

| | Sum of squares | df | Mean Square | F ratio |
|---|---|---|---|---|
| Regression | 15734041.5 | 2 | 7867020.8 | 13.16 |
| Residual | 16145357.0 | 27 | 597976.2 | |

Variables in Equation

| Variables | Regression Coefficient | Standard Error of Coefficient | Standardized Regression Coefficient (beta) | t value | p value |
|---|---|---|---|---|---|
| Intercept | 2450.2 | 579.9 | | 4.23 | <0.001 |
| Change in dietary vitamin E | −1830.7 | 362.3 | −0.746 | −5.05 | <0.001 |
| Change in intake of sucrose | 562.3 | 208.3 | 0.398 | 2.70 | 0.012 |

Example 6. Plant Stanol Ester Study

The study was a randomized, double-blind, placebo-controlled clinical intervention (Clinical Trials Register # NCT01315964) including ninety-four participant (Gylling et al. 2013). In the present study, ninety-two participants gave their consent and their samples were used for the present study. The study was performed according to the principles of the Declaration of Helsinki, and written informed consent was obtained for all study participants. The Ethics Committee of Department of the Medicine, Hospital District of Helsinki and Uusimaa approved the study protocol.

The study participants had been randomized in two groups, those who had plant stanol ester enriched rapeseed oil-based spread (3.0 g of plant stanols/day, STAEST group, n=44) and those who had the same spread without plant stanol esters (CONTROL group, n=46). The study lasted for 6 months and blood samples were collected at the baseline and at the end of the study.

LDL (d=1.019 to 1.063 g/ml) was isolated from plasma samples by sequential $D_2O$-based ultracentrifugation (Hallberg et al. 1994). LDL protein concentration was determined with Pierce™ BCA Protein Assay Kit (Thermo Scientific, Rockford, USA), and LDL was diluted to 200 µg/ml in 20 mM MES, pH 5.5, containing 150 mM NaCl and 50 µM $ZnCl_2$. LDL particle size was determined using dynamic light scattering, Wyatt DynaPro Plate Reader II (Wyatt Technology, California, USA). Human recombinant sphingomyelinase (Ruuth et al. 2019 South Asian study) was added at final concentration 200 µg/ml. Particle size was measured every 15-30 minutes for 6 hours. LDL aggregation data was collected with Dynamics V7, and data was analyzed using GraphPad Prism (version 8.0.1, GraphPad Software, La Jolla, Calif., USA).

The baseline characteristics of the study population have been reported in an article showing that LDL and non-HDL cholesterol lowered by 10% in staest group and reduced arterial stiffness in small arteries and in men also in large arteries (Gylling et al. 2013). In the present study, one subject declined to participate, and one subject could not be reached, both from staest group, and were dropped out for this reason. Baseline characteristics stayed similar and matching between the groups was not changed remarkably.

TABLE 6

Clinical characteristics of study participants. Median (range), difference between baseline and after intervention calculated with Wilcoxon signed ranks test, *p < 0.05, p < 0.01, *p < 0.001

| Clinical characteristics | Control Baseline | After intervention | Staest Baseline | After intervention |
|---|---|---|---|---|
| Subjects | 46 | | 44 | |
| male | 14 | | 20 | |
| female) | 32 | | 24 | |
| Age | 52 (24-66) | | 52 (27-66) | |
| Diabetes | 1 (2%) | | 0 | |
| Atherosclerosis | 0 | | 0 | |
| Smoking (0kk) | 1 (2%) | | 1 (2%) | |
| BMI (kg/m2) | 25.0 (17.9-34.8) | 25.4 (18.6-35.5)** | 25.1 (17.9-36.6) | 25.4 (17.9-36.3)* |
| Cholesterol (mmol/l) | 5.8 (3.5-7.1) | 5.6 (3.8-7.7)* | 5.5 (3.4-7.2) | 5.3 (3.9-7.0)* |
| LDL-C (mmol/l) | 3.6 (1.6-5.6) | 3.6 (1.6-5.4) | 3.7 (1.5-5.3) | 3.2 (1.2-5.4)*** |
| HDL-C (mmol/l) | 1.8 (0.9-2.8) | 1.8 (1.0-2.8)** | 1.7 (0.9-2.9) | 1.9 (0.8-3.2)** |
| TG-C (mmol/l) | 0.9 (0.3-2.3) | 0.9 (0.4-2.5)* | 0.8 (0.4-2.2) | 0.9 (0.4-2.5)* |
| Glucose (mmol/l) | 4.7 (4.0-6.4) | 4.9 (3.9-6.5) | 5.0 (3.8-6.0) | 4.9 (4.0-6.6) |
| hsCRP (mg/l) | 0.8 (0.2-4.0) | 0.8 (0.2-8.3) | 0.7 (0.1-3.6) | 0.8 (0.1-3.0) |
| non-HDL-C (mmol/l) | 4.0 (1.8-6.1) | 4.8 (1.8-6.1) | 3.7 (1.7-5.8) | 3.4 (1.4-5.6)*** |
| Blood pressure | | | | |
| Systolic (mmHg) | 120 (100-138) | 120 (92-138) | 124 (90-160) | 120 (100-138)** |
| Diastolic (mmHg) | 76 (60-90) | 75 (62-90) | 75 (62-90) | 75 (62-90) |
| Prot E % | 16 (10-28) | 16 (10-26) | 17 (12-25) | 17 (10-24) |
| Fat E % | 35 (16-47) | 36 (25-50) | 33 (23-50) | 35 (19-45) |
| SAFA E % | 11 (5-20) | 12 (7-21) | 11 (7-21) | 11 (5-16) |
| MUFA E % | 12 (5-23) | 12 (8-18)*** | 11 (7-20) | 13 (7-18)** |
| PUFA E % | 5 (3-13) | 5 (3-15) | 5 (3-8) | 6 (3-12)* |
| CARB E % | 41 (24-56) | 42 (26-53) | 43 (22-56) | 42 (27-54) |
| Alcohol E % | 2 (0-11) | 0 (0-15) | 0 (0-15) | 1 (0-13) |

Figure 12A:
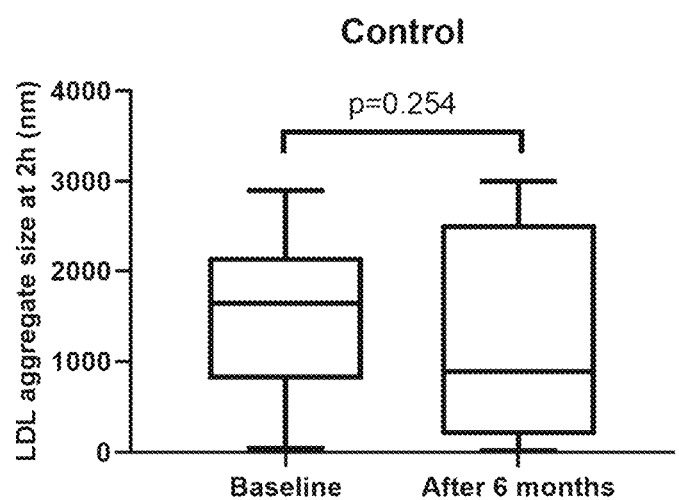
FIG. 12A. The LDL aggregation size at 2 h in control situation.
Figure 12B:
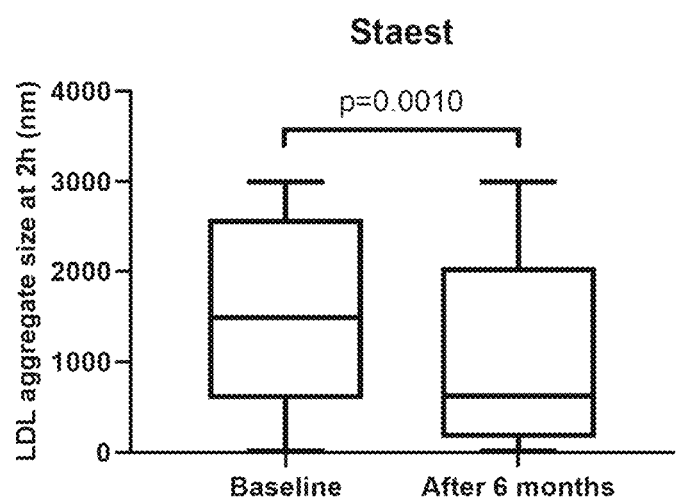
FIG. 12B. The LDL aggregation size at 2 h in staest situation.

In this study it was found that LDL aggregation susceptibility was significantly reduced in STAEST group (p=0.0010, Student's paired t-test), but not in CONTROL group after the intervention (FIGS. 12A and B). Dietary plant stanol esters could be a safe non-medical way to reduce LDL aggregation susceptibility and reduce risk for cardiovascular diseases.

Example 7. Hypercaloric Diet Study

In this study, participants were overfed 36 overweight for 3 weeks with 1000 extra kcal/day of either saturated fat (SAT), unsaturated fat (UNSAT), or simple sugars (CARB) (Luukkonen et al. 2018). Subjects in this study (ClinicalTrials.gov, NCT02133144) were recruited by advertisements or by contacting subjects who had previously participated in metabolic studies. Recruitment and screening have been described in detail previously (Luukkonen et al. 2018). Exclusion criteria included i) type 1 or 2 diabetes, ii) liver disease other than NAFLD, iii) excessive use of alcohol (over 20 g/day for women and over 30 g/day for men), iv) evidence of any other acute or chronic disease, v) extreme obesity (BMI 40 kg/m$^2$), vi) use of drugs known to influence glucose or lipid metabolism, vii) pregnancy or lactation. Written informed consent was obtained from all participants after being explained the nature and potential risks of the study. The ethics committee of the Helsinki University Hospital had approved the study protocol and study was conducted in accordance with the Declaration of Helsinki.

LDL (d=1.019 to 1.063 g/mL) was isolated from plasma samples by sequential D$_2$O-based ultracentrifugation (Hallberg et al. 1994). 300 μl of plasma was used for isolation and in the end 300 μl of LDL was collected from the top of the ultracentrifugation tube. The concentration of LDL was measured using the Pierce™ BCA Protein Assay Kit (Thermo Scientific, Rockford, USA). LDL aggregation was measured using LDL samples diluted to 200 μg of LDL/ml in 20 mM MES, pH 5.5, containing 150 mM NaCl and 50 μM ZnCl$_2$. The size of the LDL particles was measured (0 h) using dynamic light scattering (Wyatt DynaPro Plate Reader II; Wyatt Technology, California, USA). Sphingomyelinase was added to the wells and the wells were coated with paraffin. Particle aggregation was followed by measuring their size approximately every 15 minutes for 6 hours. Aggregation data was collected with Dynamics V7.

The clinical characteristics of the study subjects are described in Table 7. The groups were similar with respect to common cardiovascular disease risk factors, including BMI, blood pressure, age and plasma lipids. BMI increased similarly in all groups during overfeeding. Plasma cholesterol, LDL cholesterol (LDL-C) and HDL cholesterol (HDL-C) increased only in the SAT group (Luukkonen et al. 2018). To monitor the compliancy of the diet, the fatty acid compositions of VLDL-TAGs was measured. In the CARB and SAT groups the amount of VLDL-TAG containing saturated fatty acids was increased, in the SAT group the amount of VLDL-TAG with unsaturated fatty acids was decreased, and in the UNSAT group the amount of VLDL-TAG with unsaturated fatty acids was increased (Luukkonen et al. 2018).

TABLE 7

Clinical characteristics from study subjects. Differences between baseline and after intervention are calculated using paired Student's t-test. *p < 0.05, **p < 0.01. Data are in mean ± SD.

| Group | UNSAT | | SAT | | CARB | |
|---|---|---|---|---|---|---|
| Group size (n) | 11 | | 13 | | 12 | |
| Women (n) | 6 | | 8 | | 6 | |
| Men (n) | 5 | | 5 | | 6 | |
| Age (years) | 51 ± 10 | | 46 ± 8 | | 47 ± 11 | |
|  | Baseline | After Intervention | Baseline | After Intervention | Baseline | After Intervention |
| BMI (kg/m$^2$) | 30.6 ± 6.0 | 30.8 ± 6.1* | 29.4 ± 6.5 | 29.9 ± 6.5** | 32.8 ± 6.1 | 33.2 ± 6.0** |
| Blood pressure (mmHg) | | | | | | |
| Systolic | 133 ± 18 | 134 ± 18 | 133 ± 15 | 131 ± 18 | 139 ± 2 | 137 ± 10 |
| Diastolic | 83 ± 8 | 81 ± 11 | 80 ± 11 | 84 ± 14 | 85 ± 13 | 82 ± 8 |
| fP-Cholesterol (mmol/l) | 5.3 ± 0.8 | 5.1 ± 0.5 | 4.9 ± 1.3 | 5.4 ± 1.2** | 5.6 ± 0.7 | 5.5 ± 1.0 |
| fP-HDL-C (mmol/l) | 1.6 ± 0.5 | 1.7 ± 0.5 | 1.6 ± 0.4 | 1.9 ± 0.5** | 1.5 ± 0.4 | 1.4 ± 0.4 |
| fP-LDL-C (mmol/l) | 3.4 ± 0.8 | 3.3 ± 0.7 | 3.0 ± 1.0 | 3.3 ± 1.0** | 3.7 ± 0.7 | 3.7 ± 0.9 |
| fP-TGs (mmol/l) | 1.1 ± 0.4 | 1.3 ± 0.5 | 1.1 ± 1.0 | 1.1 ± 0.8 | 1.4 ± 0.6 | 1.4 ± 0.8 |
| fP-Glucose (mmol/l) | 5.7 ± 0.6 | 5.6 ± 0.7 | 5.6 ± 0.7 | 5.6 ± 0.6 | 5.8 ± 0.7 | 5.9 ± 0.6 |

Figure 13:
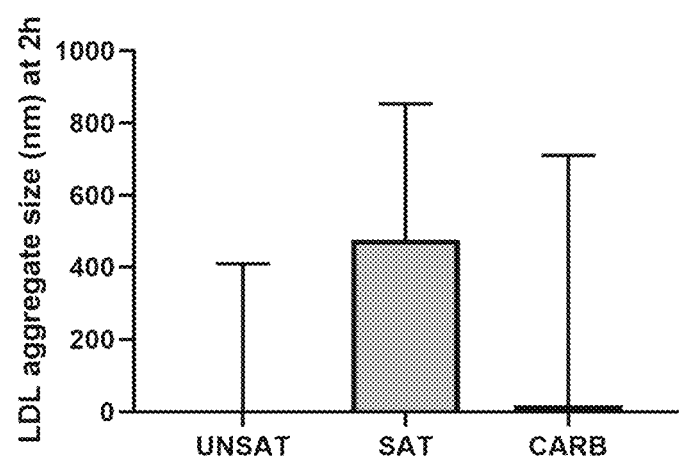
FIG. 13. The UNSAT and CARB diets do not influence the susceptibility of LDL to aggregate.

The UNSAT and CARB diets did not influence the susceptibility of LDL to aggregate. In contrast, the SAT diet significantly increased LDL aggregation (42%, p=0.003, FIG. 13).

Example 8. Ethnicity Study

Twelve healthy Dutch South Asian and twelve Dutch white Caucasian men were matched for age (18-32 years) and BMI (18-27 kg/m$^2$) and were included in this study. South Asian subjects were eligible in case of being born and raised in the Netherlands and having four grandparents from South Asian descent. Major exclusion criteria included smoking, recent weight-loss, a significant chronic disease and/or a renal, hepatic or endocrine disease. None of the participant used any medication. The study was performed in accordance with the principles of the revised declaration of Helsinki and approved by the medical ethical committee of the Leiden University Medical Center (LUMC) in the Netherlands (World Medical Association Declaration of Helsinki 2013). All study participants provided written informed consent prior to the study. This study was conducted as part of a clinical trial that investigated the effects of the glucagon-like peptide 1 receptor agonist exenatide on BAT activity and energy metabolism (Janssen & Nahon et al, in preparation, trial register number clinicaltrials.gov NCT03002675).

Table 8 shows the clinical characteristics of the participants. Compared with white Caucasians, South Asians had a higher body fat percentage (18.9±3.2 vs. 14.5±4.7%, p=0.015, unpaired student t-test) at a similar BMI (24.7±2.7 vs. 23.9±2.4 kg/m$^2$, p=0.47). There were no significant differences between ethnicities in plasma glucose and serum insulin, triglycerides, HDL-cholesterol or LDL-cholesterol, while serum total cholesterol was higher in South Asians than in white Caucasians (4.8±0.8 vs. 4.2±0.5 mmol/1, p=0.032).

TABLE 8

Clinical characteristics of study participants. Data are presented as mean ± SD. Statistical differences between the ethnicities were determined using the unpaired Student's t-test, and the p-value is reported in the case of a statistically significant difference between the South Asians and white Caucasians.

| Clinical characteristics | South Asians (n = 12) | White Caucasians (n = 12) | p-value |
|---|---|---|---|
| Age (years) | 27.5 ± 3.2 | 25.6 ± 3.2 | |
| Body mass index (kg/m$^2$) | 24.7 ± 2.7 | 23.9 ± 2.4 | |
| Body fat (%) | 18.9 ± 3.2 | 14.5 ± 4.7 | 0.015 |
| Systolic blood pressure (mmHg) | 119 ± 6 | 124 ± 9 | |
| Diastolic blood pressure (mmHg) | 75 ± 9 | 82 ± 10 | |
| Triglycerides (mmol/l) | 0.82 ± 0.41 | 0.83 ± 0.28 | |
| Total cholesterol (mmol/l) | 4.8 ± 0.8 | 4.2 ± 0.5 | 0.032 |
| HDL-cholesterol (mmol/l) | 1.19 ± 0.32 | 1.14 ± 0.24 | |
| LDL-cholesterol (mmol/l) | 3.3 ± 0.9 | 2.7 ± 0.4 | |
| Insulin (pg/ml) | 137 ± 133 | 136 ± 89 | |
| Glucose (mmol/l) | 4.8 ± 0.3 | 4.6 ± 0.2 | |

LDL (d=1.019 to 1.063 g/ml) was isolated from 300 μl plasma samples by $D_2O$-based sequential ultracentrifugation (Hallberg et al. 1994), and 300 μl of LDL was collected. The concentration of LDL is expressed as protein concentration, which was determined using Pierce™ BCA Protein Assay Kit (Thermo Scientific, Rockford, USA). The measurement of LDL aggregation susceptibility was performed essentially as described before (Ruuth et al. 2018). Briefly, isolated LDL particles were diluted to 200 μg/ml in 20 mM MES, pH 5.5, containing 150 mM NaCl and 50 μM $ZnCl_2$. The size of the LDL particles was measured (0 h) using dynamic light scattering (Wyatt DynaPro Plate Reader II; Wyatt Technology, California, USA). Sphingomyelinase was added to the wells and the wells were coated with paraffin. Particle aggregation was followed by measuring their size approximately every 15 minutes for 6 hours. Aggregation data was collected with Dynamics V7.

Figure 14A:
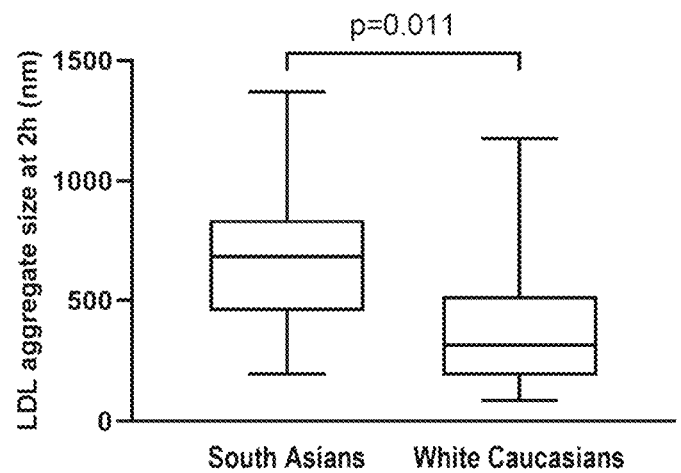
FIG. 14A. LDL from Asians aggregates more rapidly than LDL from white Caucasians, as indicated by a larger LDL aggregate size at 2 h (350±290 nm vs 620±320 nm, p=0.011).

To determine if LDL of South Asians is more prone to aggregate than LDL of white Caucasians, we isolated LDL from the plasma samples and measured LDL aggregation susceptibility. Treatment of LDL with sphingomyelinase induced rapid formation of large aggregates. There were no significant differences in the size of LDL particles in the beginning of the incubation or in the end of the incubation. However, LDL from South Asians aggregated more rapidly than LDL from white Caucasians, as indicated by a larger LDL aggregate size at 2 h (350±290 nm vs 620±320 nm, p=0.011; FIG. 14A).

Figure 14B:
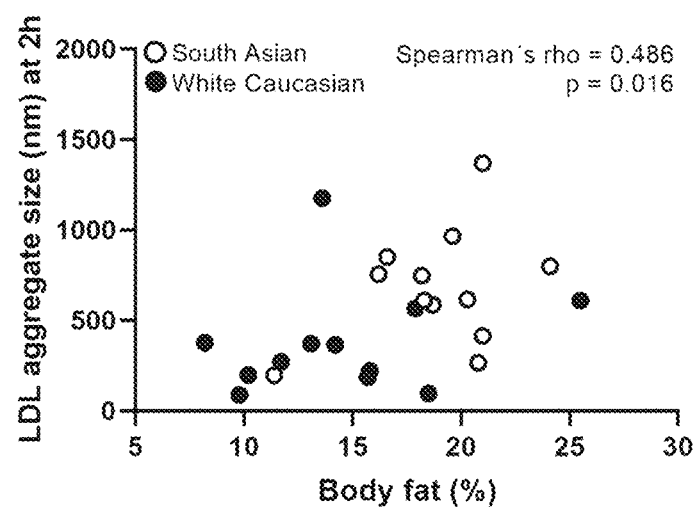
FIG. 14B. LDL aggregate size at 2 h significantly and positively correlates with body fat percentage (Spearman's rho=0.486, p=0.016).
Figure 14C:
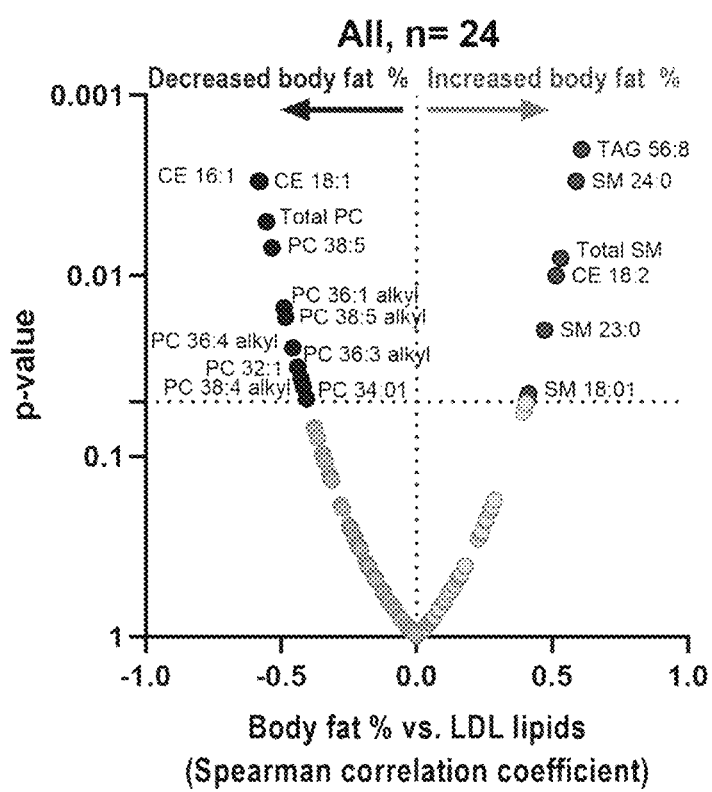
FIG. 14C. A higher body fat percentage is associated with a higher proportion of total SM and lower proportion of total PC in the surface of LDL particles.

Since obesity may modulate ASCVD risk by inducing alterations in the plasma lipidome, we next examined whether anthropometric measurements correlated with LDL lipid components and LDL aggregation. While no correlation with BMI was observed (data not shown), LDL aggregate size at 2 h significantly and positively correlated with body fat percentage (Spearman's rho=0.486, p=0.016) (FIG. 14B). Interestingly, a higher body fat percentage was associated with a higher proportion of total SM and lower proportion of total PC in the surface of LDL particles (FIG. 14C), which were previously shown to be characteristics of aggregation-prone LDL (Ruuth et al. 2018).

REFERENCES

1. Aromaa A, Koskinen S. Health and functional capacity in Finland: Baseline results of the Health 2000 health examination survey. Publications of the National Public Health Institute. 2004, B12/200.
2. Magnusdottir O K, Landberg R, Gunnarsdottir I, Cloetens L, Akesson B, Onning G, Jonsdottir S E, Rosqvist F, Schwab U, Herzig K H, Savolainen M J, Brader L, Hermansen K, Kolehmainen M, Poutanen K, Uusitupa M, Thorsdottir I, Riserus U. Plasma alkylresorcinols reflect important whole-grain components of a healthy Nordic diet. J Nutr. 2013, 143: 1383-1390.
3. Uusitupa M, Hermansen K, Savolainen M J, Schwab U, Kolehmainen M, Brader L, Mortensen L S, Cloetens L, Johansson-Persson A, Onning G, Landin-Olsson M, Herzig K H, Hukkanen J, Rosqvist F, Iggman D, Paananen J, Pulkki K J, Siloaho M, Dragsted L, Barri T, Overvad K, Bach Knudsen K E, Hedemann M S, Amer P, Dahlman I, Borge G I, Baardseth P, Ulven S M, Gunnarsdottir I, Jonsdottir S, Thorsdottir I, Oresic M, Poutanen K S, Riserus U, Akesson B. Effects of an isocaloric healthy Nordic diet on insulin sensitivity, lipid profile and inflammation markers in metabolic syndrome—a randomized study (SYSDIET). J Intern Med. 2013, 274: 52-66.
4. Baruch A, Mosesova S, Davis J D, Budha N, Vilimovskij A, Kahn R, Peng K, Cowan K J, Harris L P, Gelzleichter T, Lehrer J, Davis J C, Jr., Tingley W G. Effects of RG7652, a Monoclonal Antibody Against PCSK9, on LDL-C, LDL-C Subfractions, and Inflammatory Biomarkers in Patients at High Risk of or With Established Coronary Heart Disease (from the Phase 2 EQUATOR Study). Am J Cardiol. 2017, 119: 1576-1583.
5. Havel R J., Eder H A, Bragdon J H. The distribution and chemical composition of ultracentrifucally separated lipoproteins in human serum. J Clin Invest. 1955, 34: 1345-1355.
6. Folch J, Lees M, Sloane Stanley G H. A simple method for the isolation and purification of total lipides from animal tissues. J Biol Chem. 1957, 226: 497-509.
7. Haimi P, Uphoff A, Hermansson M, Somerharju P. Software tools for analysis of mass spectrometric lipidome data. Anal Chem. 2006, 78: 8324-8331.
8. Hsu F F, Turk J. Structural determination of glycosphingolipids as lithiated adducts by electrospray ionization mass spectrometry using low-energy collisional-activated dissociation on a triple stage quadrupole instrument. J Am Soc Mass Spectrom. 2001, 12: 61-79.
9. Houjou T, Yamatani K, Nakanishi H, Imagawa M, Shimizu T, Taguchi R. Rapid and selective identification of molecular species in phosphatidylcholine and sphingomyelin by conditional neutral loss scanning and MS3. Rapid Commun Mass Spectrom. 2004, 18: 3123-3130.
10. Kauhanen D, Sysi-Aho M, Koistinen K M, Laaksonen R, Sinisalo J, Ekroos K. Development and validation of a high-throughput LC-MS/MS assay for routine measurement of molecular ceramides. Anal Bioanal Chem. 2016, 408: 3475-3483.
11. Sneck M, Nguyen S D, Pihlajamaa T, Yohannes G, Riekkola M L, Milne R, Kovanen P T, Oorni K. Conformational changes of apoB-100 in SMase-modified LDL mediate formation of large aggregates at acidic pH. J Lipid Res. 2012, 53: 1832-1839.
12. Nguyen S D, Oorni K, Lee-Rueckert M, Pihlajamaa T, Metso J, Jauhiainen M, Kovanen P T. Spontaneous remodeling of HDL particles at acidic pH enhances their capacity to induce cholesterol efflux from human macrophage foam cells. J Lipid Res. 2012, 53: 2115-2125.
13. Laajala T D, Jumppanen M, Huhtaniemi R, Fey V, Kaur A, Knuuttila M, Aho E, Oksala R, Westermarck J, Makela S, Poutanen M, Aittokallio T. Optimized design and analysis of preclinical intervention studies in vivo. Sci Rep. 2016, 6: 30723.
14. Gylling, H., et al., *The effects of plant stanol ester consumption on arterial stiffness and endothelial function in adults: a randomised controlled clinical trial*. BMC Cardiovasc Disord, 2013. 13: p. 50.
15. Hallberg, C., et al., *Lipoprotein fractionation in deuterium oxide gradients: a procedure for evaluation of antioxidant binding and susceptibility to oxidation*. J Lipid Res, 1994. 35(1): p. 1-9.
16. Luukkonen, P. K., et al., *Saturated Fat Is More Metabolically Harmful for the Human Liver Than Unsaturated Fat or Simple Sugars*. Diabetes Care, 2018. 41 (8): p. 1732-1739.
17. *World Medical Association Declaration of Helsinki: ethical principles for medical research involving human subjects*. JAMA, 2013. 310(20): p. 2191-4.
18. Ruuth, M., et al., *Susceptibility of low-density lipoprotein particles to aggregate depends on particle lipidome, is modifiable, and associates with future cardiovascular deaths*. Eur Heart J, 2018. 39(27): p. 2562-2573.

The invention claimed is:

1. A method of determining a presence or risk of an atherosclerotic cardiovascular disease (ASCVD) or a cardiometabolic disease in a human subject, the method comprising:
providing LDL particles from a blood plasma or serum sample of the human subject;
mixing the LDL particles with a sphingomyelinase enzyme in a solution at acidic pH;
detecting formation of LDL aggregates in the solution, and
measuring the sizes of the detected LDL aggregates,
wherein the detected LDL aggregates have a median size of at least 200 nm and the human subject is determined to have or be at risk for developing an ASCVD or a cardiometabolic disease.

2. The method of claim 1, wherein the step of providing LDL particles from a human blood plasma or serum sample comprises isolating LDL particles from the human plasma or serum sample by ultracentrifugation.

3. The method of claim 1, further comprising, prior to mixing, determining the size of the LDL particles.

4. The method of claim 1, wherein the acidic pH is a pH of between 5 and 6.

5. The method of claim 1, comprising mixing the LDL particles with the sphingomyelinase enzyme in a solution at acidic pH at a temperature of about 30-40° C.

6. The method of claim 1, comprising detecting formation of LDL aggregates in the solution using dynamic light scattering (DLS) or UV-vis absorbance spectroscopy.

7. The method of claim 1, comprising measuring the size of the detected LDL aggregates every 15 to 30 minutes for up to 6 hours after mixing the LDL particles with the sphingomyelinase enzyme.

8. The method of claim 1, comprising measuring the size of the detected LDL aggregates about 2 hours after mixing the LDL particles with the sphingomyelinase enzyme.

9. The method of claim 1, wherein the human subject is administered a treatment for ASCVD or cardiometabolic disease.

10. The method of claim 1, comprising administering to the human subject a food, diet, or supplement comprising a plant stanol or plant stanol ester.

11. A method comprising:
providing a human plasma or serum sample;
mixing the human plasma or serum sample with a sphingomyelinase enzyme at acidic pH;
detecting formation of LDL aggregates in the sample, and measuring the sizes of the detected LDL aggregates.

12. The method of claim 11, wherein the detected LDL aggregates have a median size of at least 200 nm.

13. A method comprising:
providing LDL particles from a blood plasma sample of a human subject that has been taking a cholesterol lowering medication selected from the group consisting of HMG CoA reductase inhibitor, a selective cholesterol absorption inhibitor, and a bile-acid binding resin;
mixing the LDL particles with sphingomyelinase enzyme in a solution at acidic pH;
detecting formation of LDL aggregates in said solution;
measuring the sizes of the detected LDL aggregates; and
if the LDL aggregates have a median size of at least 500 nm, continue administering to the human subject a therapeutically effective amount of the cholesterol lowering medication in combination with a healthy Nordic diet, a low sucrose diet, or a Proprotein Convertase Subtilisin/Kexin type 9 (PCSK9) inhibitor; and
if the LDL aggregates have a median size of below 500 nm, continue administering to the human subject a therapeutically effective amount of the cholesterol lowering medication.

14. The method of claim 13, further comprising administering to the human subject regardless of the median size of LDL aggregates a food, diet, or supplement comprising a plant stanol or plant stanol ester.

15. The method of claim 14, wherein the plant stanol or plant stanol ester is administered to the human subject at an amount of 1 gram to 3 grams daily.

16. The method of claim 13, wherein the human subject has an ASCVD or a cardiometabolic disease.

17. A method comprising:
providing LDL particles from a blood plasma sample of a human subject that has been taking a cholesterol lowering medication selected from the group consisting of HMG CoA reductase inhibitor, a selective cholesterol absorption inhibitor, and a bile-acid binding resin;
mixing the LDL particles with sphingomyelinase enzyme in a solution at acidic pH;
detecting formation of LDL aggregates in said solution;
measuring the sizes of the detected LDL aggregates; and
if the LDL aggregates have a median size of at least 500 nm, continue administering to the human subject a therapeutically effective amount of the cholesterol lowering medication in combination with a healthy Nordic diet, a PCSK9 inhibitor, or a plant stanol or plant stanol ester; and
if the LDL aggregates have a median size of below 500 nm, continue administering to the human subject a therapeutically effective amount of the cholesterol lowering medication.

18. A method comprising:
providing LDL particles from blood plasma or serum samples of (a) a human subject at risk for developing ASCVD or a cardiometabolic disease and (b) a control human subject who is known to not have ASCVD or a cardiometabolic disease;
mixing the LDL particles with a sphingomyelinase enzyme in a solution at acidic pH;
detecting formation of LDL aggregates in the solution;
measuring the sizes of the detected LDL aggregates every 15 to 30 minutes for up to 6 hours after mixing the LDL particles with the sphingomyelinase enzyme, and
comparing the sizes of the detected LDL aggregates of the human subject at risk for developing ASCVD or a cardiometabolic disease with the sizes of LDL aggregates of the control human subject.

* * * * *

SEQUENCE LISTING

<160> NUMBER OF SEQ ID NOS: 2

<210> SEQ ID NO 1
<211> LENGTH: 664
<212> TYPE: PRT
<213> ORGANISM: Homo sapiens

<400> SEQUENCE: 1

```
Ser Gly Val Pro Gly Ala Ala Arg Gly Pro Glu Gly Trp Leu Gly Ser
 1               5                  10                  15

Arg Pro Gly Gly Thr Gly Gln Thr Asn Gln Pro Arg Val Gly Ser Ala
             20                  25                  30

Thr Met Pro Arg Tyr Gly Ala Ser Leu Arg Gln Ser Cys Pro Arg Ser
         35                  40                  45

Gly Arg Glu Gln Gly Gln Asp Gly Thr Ala Gly Ala Pro Gly Leu Leu
     50                  55                  60

Trp Met Gly Leu Ala Leu Ala Leu Ala Leu Ala Leu Ala Leu Ala Leu
 65                  70                  75                  80

Ala Leu Ser Asp Ser Arg Val Leu Trp Ala Pro Ala Glu Ala His Pro
                 85                  90                  95

Leu Ser Pro Gln Gly His Pro Ala Arg Leu His Arg Ile Val Pro Arg
             100                 105                 110

Leu Arg Asp Val Phe Gly Trp Gly Asn Leu Thr Cys Pro Ile Cys Lys
         115                 120                 125

Gly Leu Phe Thr Ala Ile Asn Leu Gly Leu Lys Lys Glu Pro Asn Val
     130                 135                 140

Ala Arg Val Gly Ser Val Ala Ile Lys Leu Cys Asn Leu Leu Lys Ile
145                 150                 155                 160

Ala Pro Pro Ala Val Cys Gln Ser Ile Val His Leu Phe Glu Asp Asp
                 165                 170                 175

Met Val Glu Val Trp Arg Arg Ser Val Leu Ser Pro Ser Glu Ala Cys
             180                 185                 190

Gly Leu Leu Leu Gly Ser Thr Cys Gly His Trp Asp Ile Phe Ser Ser
         195                 200                 205

Trp Asn Ile Ser Leu Pro Thr Val Pro Lys Pro Pro Lys Pro Pro
     210                 215                 220

Ser Pro Pro Ala Pro Gly Ala Pro Val Ser Arg Ile Leu Phe Leu Thr
225                 230                 235                 240

Asp Leu His Trp Asp His Asp Tyr Leu Glu Gly Thr Asp Pro Asp Cys
                 245                 250                 255

Ala Asp Pro Leu Cys Cys Arg Arg Gly Ser Gly Leu Pro Pro Ala Ser
             260                 265                 270

Arg Pro Gly Ala Gly Tyr Trp Gly Glu Tyr Ser Lys Cys Asp Leu Pro
         275                 280                 285

Leu Arg Thr Leu Glu Ser Leu Leu Ser Gly Leu Gly Pro Ala Gly Pro
     290                 295                 300

Phe Asp Met Val Tyr Trp Thr Gly Asp Ile Pro Ala His Asp Val Trp
305                 310                 315                 320

His Gln Thr Arg Gln Asp Gln Leu Arg Ala Leu Thr Thr Val Thr Ala
                 325                 330                 335

Leu Val Arg Lys Phe Leu Gly Pro Val Pro Val Tyr Pro Ala Val Gly
             340                 345                 350

Asn His Glu Ser Thr Pro Val Asn Ser Phe Pro Pro Phe Ile Glu
         355                 360                 365

Gly Asn His Ser Ser Arg Trp Leu Tyr Glu Ala Met Ala Lys Ala Trp
     370                 375                 380

Glu Pro Trp Leu Pro Ala Glu Ala Leu Arg Thr Leu Arg Ile Gly Gly
385                 390                 395                 400

Phe Tyr Ala Leu Ser Pro Tyr Pro Gly Leu Arg Leu Ile Ser Leu Asn
                 405                 410                 415
```

Met Asn Phe Cys Ser Arg Glu Asn Phe Trp Leu Leu Ile Asn Ser Thr
            420                 425                 430

Asp Pro Ala Gly Gln Leu Gln Trp Leu Val Gly Glu Leu Gln Ala Ala
            435                 440                 445

Glu Asp Arg Gly Asp Lys Val His Ile Ile Gly His Ile Pro Pro Gly
            450                 455                 460

His Cys Leu Lys Ser Trp Ser Trp Asn Tyr Tyr Arg Ile Val Ala Arg
465                 470                 475                 480

Tyr Glu Asn Thr Leu Ala Ala Gln Phe Phe Gly His Thr His Val Asp
            485                 490                 495

Glu Phe Glu Val Phe Tyr Asp Glu Glu Thr Leu Ser Arg Pro Leu Ala
            500                 505                 510

Val Ala Phe Leu Ala Pro Ser Ala Thr Thr Tyr Ile Gly Leu Asn Pro
            515                 520                 525

Gly Tyr Arg Val Tyr Gln Ile Asp Gly Asn Tyr Ser Gly Ser Ser His
            530                 535                 540

Val Val Leu Asp His Glu Thr Tyr Ile Leu Asn Leu Thr Gln Ala Asn
545                 550                 555                 560

Ile Pro Gly Ala Ile Pro His Trp Gln Leu Leu Tyr Arg Ala Arg Glu
            565                 570                 575

Thr Tyr Gly Leu Pro Asn Thr Leu Pro Thr Ala Trp His Asn Leu Val
            580                 585                 590

Tyr Arg Met Arg Gly Asp Met Gln Leu Phe Gln Thr Phe Trp Phe Leu
            595                 600                 605

Tyr His Lys Gly His Pro Pro Ser Glu Pro Cys Gly Thr Pro Cys Arg
            610                 615                 620

Leu Ala Thr Leu Cys Ala Gln Leu Ser Ala Arg Ala Asp Ser Pro Ala
625                 630                 635                 640

Leu Cys Arg His Leu Met Pro Asp Gly Ser Leu Pro Glu Ala Gln Ser
            645                 650                 655

Leu Trp Pro Arg Pro Leu Phe Cys
            660

<210> SEQ ID NO 2
<211> LENGTH: 2452
<212> TYPE: DNA
<213> ORGANISM: Homo sapiens

<400> SEQUENCE: 2

```
ggaagaggaa gggcggagc tgctttgcgg ccggccgcgg agcagtcagc cgactacaga      60
gaagggtaat cgggtgtccc cggcgccgcc cggggccctg agggctggct agggtccagg     120
ccggggggga cgggacagac gaaccagccc cgtgtaggaa gcgcgacaat gccccgctac    180
ggagcgtcac tccgccagag ctgccccagg tccggccggg agcagggaca agacgggacc    240
gccggagccc ccggactcct ttggatgggc tggcgctgg cgctggcgct ggcgctggcg     300
ctggcgctgg ctctgtctga ctctcgggtt tctgggctc cggcagaggc tcaccctctt     360
tctccccaag gccatcctgc caggttacat cgcatagtgc cccggctccg agatgtcttt    420
gggtggggga acctcacctg cccaatctgc aaaggtctat tcaccgccat caacctcggg    480
ctgaagaagg aacccaatgt ggctcgcgtg gctccgtgg ccatcaagct gtgcaatctg    540
ctgaagatag caccacctgc cgtgtgccaa tccattgtcc acctctttga ggatgacatg    600
gtggaggtgt ggagacgctc agtgctgagc ccatctgagg cctgtggcct gctcctgggc    660
tccacctgtg ggcactggga cattttctca tcttggaaca tctctttgcc tactgtgccg    720
```

-continued

```
aagccgcccc ccaaaccccc tagccccccca gccccaggtg ccctgtcag ccgcatcctc    780
ttcctcactg acctgcactg ggatcatgac tacctggagg gcacggaccc tgactgtgca    840
gacccactgt gctgccgccg gggttctggc ctgccgcccg catcccggcc aggtgccgga    900
tactggggcg aatacagcaa gtgtgacctg cccctgagga ccctggagag cctgttgagt    960
gggctgggcc cagccggccc ttttgatatg gtgtactgga caggagacat ccccgcacat   1020
gatgtctggc accagactcg tcaggaccaa ctgcgggccc tgaccaccgt cacagcactt   1080
gtgaggaagt tcctggggcc agtgccagtg taccctgctg tgggtaacca tgaaagcaca   1140
cctgtcaata gcttccctcc cccttcatt gagggcaacc actcctcccg ctggctctat    1200
gaagcgatgg ccaaggcttg ggagccctgg ctgcctgccg aagccctgcg caccctcaga   1260
attggggggt tctatgctct ttccccatac cccggtctcc gcctcatctc tctcaatatg   1320
aattttttgtt cccgtgagaa cttctggctc ttgatcaact ccacggatcc cgcaggacag   1380
ctccagtggc tggtgggga gcttcaggct gctgaggatc gaggagacaa agtgcatata   1440
attggccaca ttcccccagg gcactgtctg aagagctgga gctggaatta ttaccgaatt   1500
gtagccaggt atgagaacac cctggctgct cagttctttg gccacactca tgtggatgaa   1560
tttgaggtct tctatgatga agagactctg agccggccgc tggctgtagc cttcctggca   1620
cccagtgcaa ctacctacat cggccttaat cctggttacc gtgtgtacca aatagatgga   1680
aactactccg ggagctctca cgtggtcctg gaccatgaga cctacatcct gaatctgacc   1740
caggcaaaca taccgggagc cataccgcac tggcagcttc tctacagggc tcgagaaacc   1800
tatgggctgc ccaacacact gcctaccgcc tggcacaacc tggtatatcg catgcggggc   1860
gacatgcaac ttttccagac cttctggttt ctctaccata agggccaccc accctcggag   1920
ccctgtggca cgccctgccg tctggctact ctttgtgccc agctctctgc ccgtgctgac   1980
agccctgctc tgtgccgcca cctgatgcca gatgggagcc tcccagaggc ccagagcctg   2040
tggccaaggc cactgttttg ctagggcccc agggcccaca tttgggaaag ttcttgatgt   2100
aggaaagggt gaaaagccc aaatgctgct gtggttcaac caggcaagat catccggtga   2160
aagaaccagt ccctgggccc caaggatgcc ggggaaacag gaccttctcc tttcctggag   2220
ctggtttagc tggatatggg aggggttttg gctgcctgtg cccaggagct agactgcctt   2280
gaggctgctg tcctttcaca gccatggagt agaggcctaa gttgacactg ccctgggcag   2340
acaagacagg agctgtcgcc ccaggcctgt gctgcccagc caggaaccct gtactgctgc   2400
tgcgacctga tgctgccagt ctgttaaaat aaagataaga gacttggact cc           2452
```